(12) United States Patent
Caldwell et al.

(10) Patent No.: US 10,598,662 B2
(45) Date of Patent: Mar. 24, 2020

(54) DIAGNOSTIC ASSAYS AND METHODS OF TREATING PNEUMONIA, SEPSIS AND SYSTEMIC INFLAMMATORY RESPONSE SYNDROME

(71) Applicant: University of Cincinnati, Cincinnati, OH (US)

(72) Inventors: Charles C. Caldwell, Cincinnati, OH (US); Kevin R. Kasten, Cincinnati, OH (US); Priya S. Prakash, Cincinnati, OH (US); Bobby L. Johnson, III, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 16/050,004

(22) Filed: Jul. 31, 2018

(65) Prior Publication Data
US 2019/0056397 A1 Feb. 21, 2019

Related U.S. Application Data

(62) Division of application No. 14/092,443, filed on Nov. 27, 2013, now Pat. No. 10,073,097.

(60) Provisional application No. 61/781,488, filed on Mar. 14, 2013, provisional application No. 61/730,669, filed on Nov. 28, 2012.

(51) Int. Cl.
| | | |
|---|---|---|
| *G01N 33/53* | (2006.01) | |
| *G01N 33/569* | (2006.01) | |
| *A61K 31/7048* | (2006.01) | |
| *A61K 31/395* | (2006.01) | |
| *A61K 31/43* | (2006.01) | |
| *A61K 31/431* | (2006.01) | |
| *A61K 31/4706* | (2006.01) | |
| *A61K 31/496* | (2006.01) | |
| *A61K 31/545* | (2006.01) | |
| *A61K 31/546* | (2006.01) | |
| *A61K 31/65* | (2006.01) | |
| *A61K 31/7052* | (2006.01) | |

(52) U.S. Cl.
CPC ..... *G01N 33/56972* (2013.01); *A61K 31/395* (2013.01); *A61K 31/43* (2013.01); *A61K 31/431* (2013.01); *A61K 31/4706* (2013.01); *A61K 31/496* (2013.01); *A61K 31/545* (2013.01); *A61K 31/546* (2013.01); *A61K 31/65* (2013.01); *A61K 31/7048* (2013.01); *A61K 31/7052* (2013.01); *G01N 2333/70503* (2013.01); *G01N 2800/12* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 2009/0192434 | A1* | 7/2009 | Thorn | C07K 16/28 604/6.03 |
| 2013/0011863 | A1* | 1/2013 | Hirsch | C07K 16/28 435/7.92 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Daniel et al., Increase of circulating neutrophil and platelet microparticles during acute vasculitis and hemodialysis. Kidney International, 2006, 69, pp. 1416-1423. (Year: 2006).*
Prakash et al., Human Microparticles generated during sepsis in patients with critical illness are neutrophil-derived and modulate the immune response, J Trauma Acute Care Surg, vol. 73, No. 2, Aug. 2012, pp. 401-407. (Year: 2012).*
Introduction to Flow Cytometry: A Learning Guide, Dec. 2002, pp. 1-52 (Year: 2002).*
Priya Prakash MD et al, "Human Microparticles Generated During Sepsis in Critically Ill Patients are Neutrophil-Derived and Modulate the Immune System," Paper 5, Session 10:10 a.m., Jan. 11, 2012, Eastern Association for the Surgery of Trauma (EAST), 25th Annual Scientific Assembly, Lake Buena Vista, Florida.
Johnson, Bobby L. et al, "Mechanisms underlying mouse TNF-α stimulated neutrophil derived micropartile generation"; Biochemical and Biophysical Research Communications 437 (2013) 591-596.

* cited by examiner

*Primary Examiner* — Gary Counts
(74) *Attorney, Agent, or Firm* — Dinsmore & Shohl LLP

(57) ABSTRACT

An in vitro method for diagnosing and treating sepsis in a patient is provided, the method including: contacting at least a portion of a biological sample from the patient consisting essentially of microparticles isolated via differential centrifugation with reagents for detection and/or quantification of neutrophil-derived microparticles; determining a level of neutrophil-derived microparticles based on the contacting step; diagnosing sepsis in the patient when the determined level of neutrophil-derived microparticles is elevated relative to a cutoff value of the neutrophil-derived microparticles; and treating the diagnosed patient for sepsis.

15 Claims, 24 Drawing Sheets

DIAGNOSTIC ASSAYS AND METHODS OF TREATING PNEUMONIA, SEPSIS AND SYSTEMIC INFLAMMATORY RESPONSE SYNDROME

PRIORITY CLAIM

The present application is a divisional of U.S. application Ser. No. 14/092,443, filed Nov. 27, 2013, now U.S. Pat. No. 10,073,097, and claims priority to U.S. Provisional application ser. No. 61/730,669, filed Nov. 28, 2012, and U.S. Provisional application Ser. No. 61/781,488, filed Mar. 14, 2013, the full disclosures of which are incorporated in their entirety herein by this reference.

TECHNICAL FIELD

The present disclosure relates to methods for diagnosing and treating pneumonia, sepsis and systemic inflammatory response syndrome, and to diagnostic kits. More specifically, the present disclosure relates to methods for diagnosing and treating pneumonia and sepsis by determining a level of neutrophil-derived microparticles (NDMP) and/or by modulating concentrations of NDMP in bronchial, and to diagnostic kits for assessing pneumonia and sepsis.

BACKGROUND

Pneumonia is one of the most common nosocomial infections, causing significant morbidity and mortality in the United States for patients in the intensive care unit and extending hospitalization costing billions of dollars annually. Currently, the gold standard for the diagnosis of pneumonia is based upon results from a bacterial culture. This process takes approximately 72 hours. During this 72 hour waiting period, the patient is empirically administered broad-spectrum antibiotics.

Sepsis is the leading cause of morbidity and mortality in surgical intensive care units. Despite recent advances in treatment and management, about 1.1 million hospitalized patients develop sepsis annually in the United States, with an accompanying annual mortality rate of 28.6%. Sepsis and its associated complications remain an enormous economic burden on the health care system, with total annual costs exceeding $1.4 billion USD nationally. Due to several high-profile fatalities, the high mortality rates in general, and high associated costs, sepsis continues to remain a serious concern to health-care providers.

While clinical and experimental studies have dramatically increased the understanding of the pathogenesis of both pneumonia and sepsis, the standard of care remains largely supportive, coupled with the use of antibiotics. With an increasing number of patients becoming infected with antibiotic-resistant bacteria, novel non-antibiotic treatments are urgently needed to combat pneumonia and sepsis.

During pneumonia and sepsis, exquisite control of the inflammatory response is necessary to promote an anti-microbial response and minimize tissue injury. Activated leukocytes are essential for the anti-microbial response, but can become unresponsive or undergo apoptosis over the course of these infections. In other inflammatory states, both activated and apoptotic leukocytes have been shown to generate microparticles (hereinafter "MPs"). Although MPs are normally found in the circulation of healthy individuals, changes in the quantity and type of circulating MPs have been observed in individuals with ongoing inflammation.

At the onset, lung bacterial infection and sepsis are both characterized by robust leukocyte recruitment and the release of inflammatory mediators, which in pneumonia are responsible for alveolar damage, edema, and impaired oxygen transport, and in sepsis are response fro hypoperfusion and organ dysfunction. As the disease state persists, a shift towards an anti-inflammatory state is observed, and patients can develop features consistent with immune suppression. An important hallmark of immune suppression is profound immune cell apoptosis. One consequence of this is ingestion of apoptotic, phosphatidyl serine-expressing bodies by phagocytes and the subsequent secretion of anti-inflammatory cytokines such as TGF-$\beta$, $PGE_2$ and IL-10. Thus, leukocyte apoptosis and ingestion can lead to a reduced number of cells available for mounting an anti-microbial response as well as increasing levels of anti-inflammatory cytokines. This immune suppression, coupled with increasing cases with antibiotic resistant bacteria, represent a significant risk for increased mortality and morbidity for patients in intensive care units.

One possible inflammatory mediator of infection is MPs. MPs have long been termed "platelet dust" and considered inert debris reflecting cellular activation or damage. MPs are small intact vesicles derived from cell membranes and vary in size from 0.3-1.0 μm. The most studied MPs in the blood are derived from platelets, although peripheral and tissue MPs can also arise from lymphocytes, myeloid cells, endothelial cells, and red blood cells. MPs are easily separated and distinct from exosomes and cellular debris by differential centrifugation. MPs display membrane proteins implicated in a variety of fundamental processes and thus may constitute a disseminated pool of bioactive effectors. They are thought to contribute to hemostatic and inflammatory responses, vascular remodeling and angiogenesis, cell survival, and apoptosis.

Activation and cellular death are the proposed methods of MP generation, though the exact mechanisms of these processes are still unclear. During cell activation, remodeling of the plasma membrane can take place. This membrane modification can cause bleb formation, leading to the extrusion of MPs which incorporate surface proteins and other contents of the originating cell. MP release is also associated with cell apoptosis and may occur at the same time as cell fragmentation and the formation of apoptotic bodies.

Septic shock is characterized by an overwhelming release of inflammatory mediators, which are responsible for organ dysfunction and hypoperfusion. However, as sepsis persists, a shift towards an anti-inflammatory state is observed, and patients develop features consistent with immune suppression. Interestingly, 70% of septic non-survivors are still alive 3 days after the onset of the pro-inflammatory phase of septic shock. Approximately 80% of septic non-survivors had a continuous septic focus at time of death. Taken together, it is believed that the majority of shock-related deaths occur during this immune-compromised state in which the ability to eradicate infectious microorganisms is reduced. An important hallmark of immune suppression is profound immune cell apoptosis. One consequence of this is ingestion of apoptotic, phosphatidyl serine-expressing bodies by phagocytes and the subsequent secretion of anti-inflammatory cytokines such as TGF-$\beta$, $PGE_2$ and IL-10. Leukocyte apoptosis and ingestion can lead to a reduced number of cells available for mounting an anti-microbial response as well as increasing levels of anti-inflammatory cytokines. This immune suppression, coupled with increasing cases with antibiotic-resistant bacteria, represent a significant risk for increased mortality and morbidity for patients in intensive care units.

The ineffectiveness of current interventions to better ameliorate the impact of sepsis upon patients in the intensive care unit demonstrates that more knowledge of the pathophysiology of sepsis is needed to develop more successful therapies. While studies have dramatically increased the understanding of sepsis pathogenesis, the standard of care remains largely supportive.

SUMMARY

The present disclosure is based in part on the discovery that neutrophil-derived microparticles (hereinafter "NDMPs") are increased in response to pneumonia and/or sepsis. Accordingly, in one embodiment, methods for diagnosing pneumonia and/or sepsis are disclosed In certain embodiments, in vitro methods for assessing pneumonia or sepsis in a patient are disclosed. The methods include (a) contacting at least a portion of a biological sample from the patient with reagents for detection and/or quantification of NDMPs. The method also includes (b) determining a level of NDMPs based on the contacting in step (a). Additionally, the method includes (c) assessing as indicating pneumonia or sepsis in the patient if the determined level of NDMPs is elevated relative to a cutoff value of the NDMPs.

In another embodiment, a method for managing treatment of a patient suspected of having pneumonia is disclosed. The method includes (a) assessing pneumonia in vitro in the patient by calculating a concentration of NDMPs, wherein an elevated concentration of NDMPs relative to a cutoff value of NDMPs is indicative of pneumonia. The method also includes (b) treating the patient for pneumonia where pneumonia is indicated in step (a), wherein the calculated concentration of NDMPs is elevated. Additionally, the method includes (c) placing the patient under active surveillance where pneumonia is not indicated in step (a), wherein the calculated concentration of NDMPs is not elevated.

In other embodiments, methods of managing treatment in a patient suffering from pneumonia or sepsis are disclosed. The methods include (a) establishing a baseline concentration of NDMPs in either a bronchoalveolar lavage fluid sample or an abdominal fluid sample, respectively, from the patient, (b) initiating treatment, and (c) serially monitoring a concentration of NDMPs in the patient during the treatment, wherein the treatment is managed to decrease the concentration of NDMPs in the patient.

According to other embodiments, methods of treating a disordered immune response, for example sepsis, pneumonia or systemic inflammatory response syndrome, in a patient are provided. The methods comprise modulating a concentration of neutrophil-derived microparticles (NDMP) in a sample from the patient and administering agents or initiating treatments effective to either increase or decrease generation of NDMP in the patient, depending on the modulation sought to be effectuated.

These and other embodiments and aspects of the invention will be more clearly understood by reference to the Figures and following description, however the description and Figures are understood to illustrate by example and should not be construed to limit the scope of the invention as defined by the claims.

Figure 11:
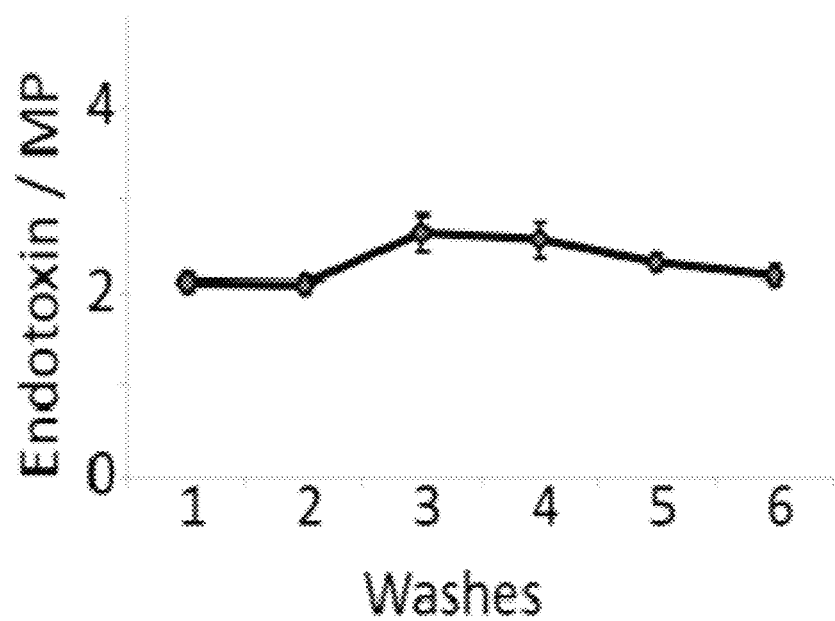
Figure 12:
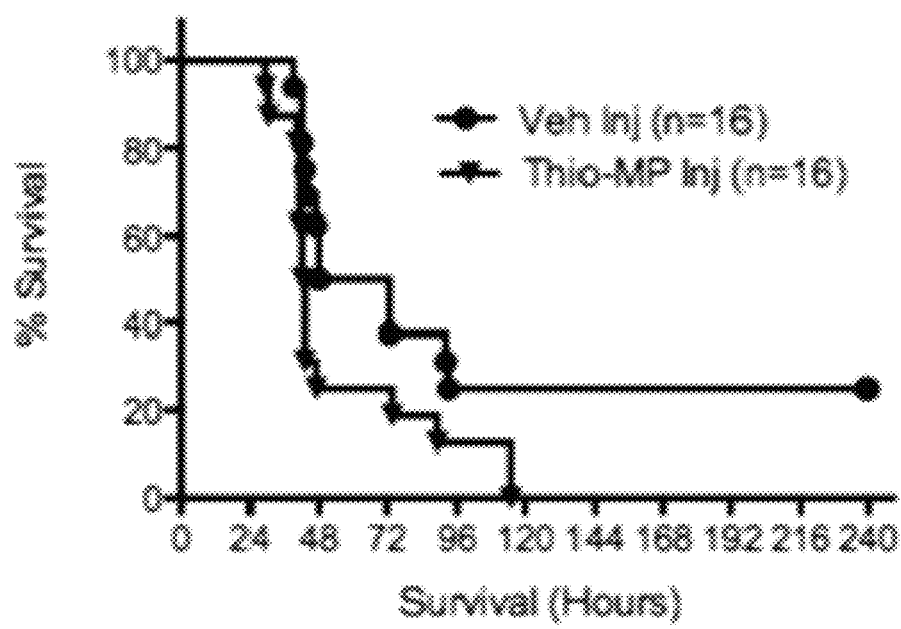
Figure 13:
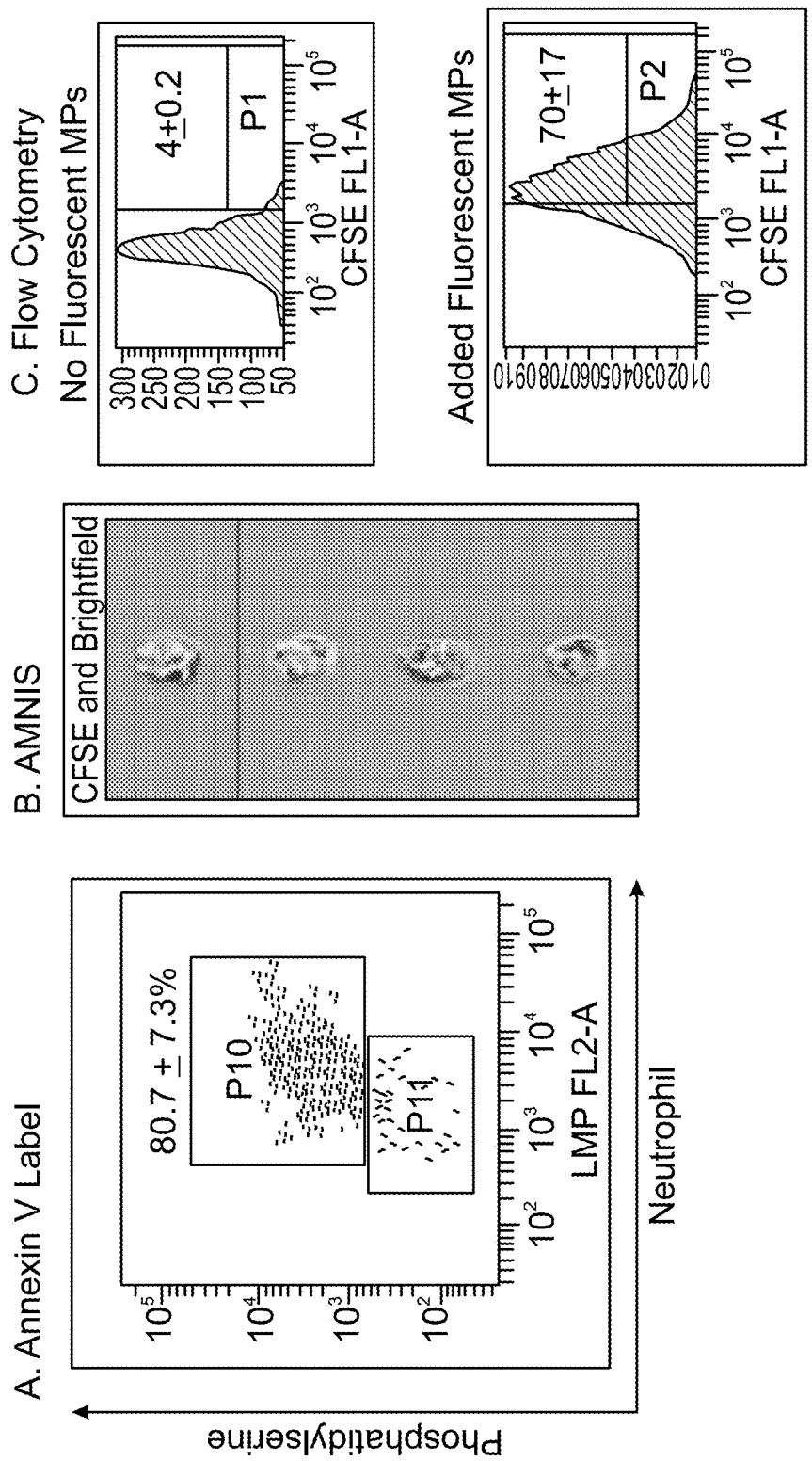
Figure 14:
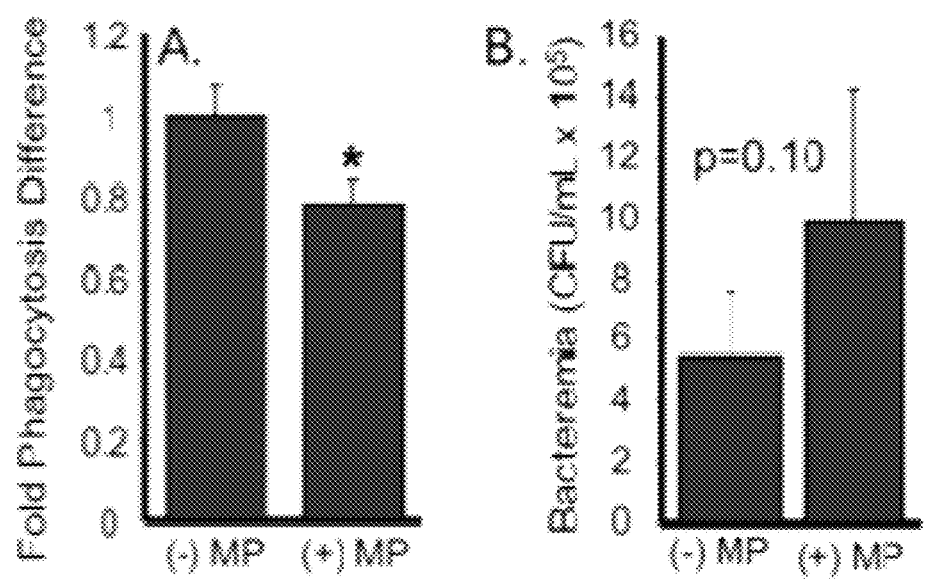
Figure 15:
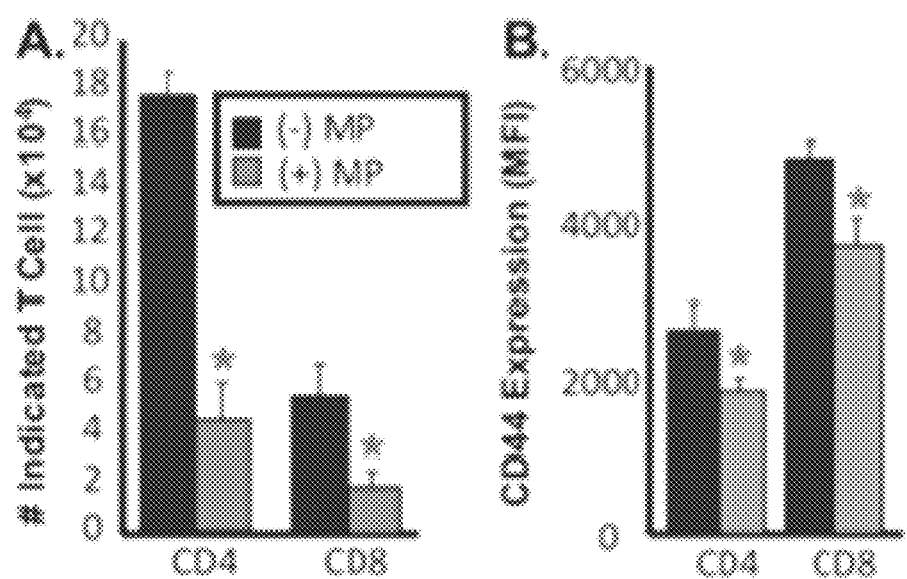
Figure 16:
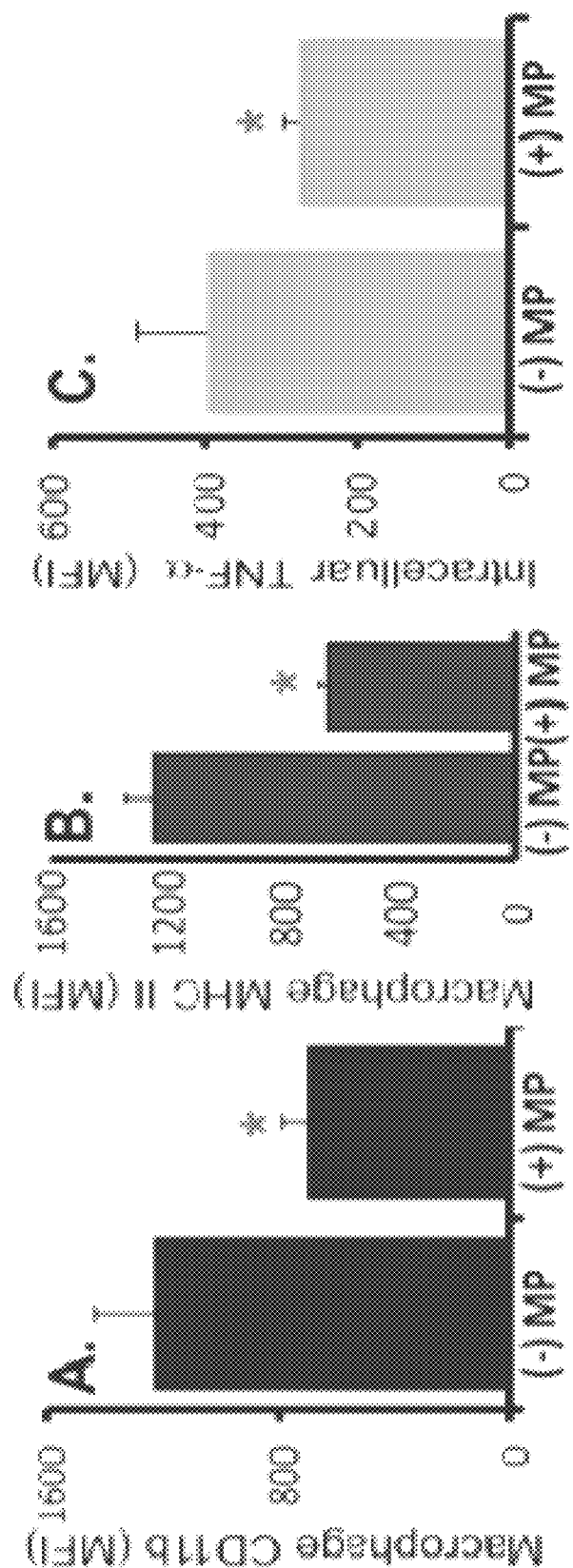
Figure 17:
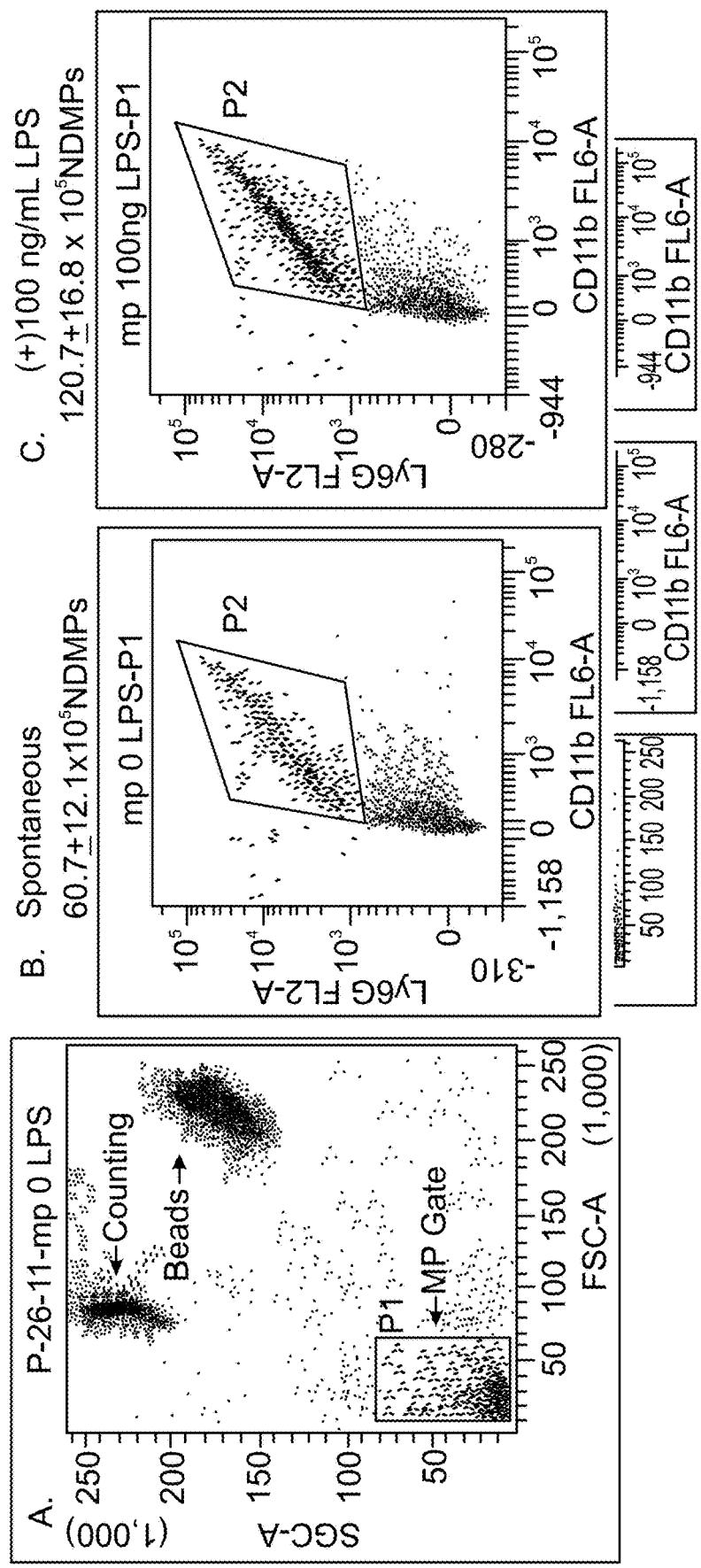
Figure 18:
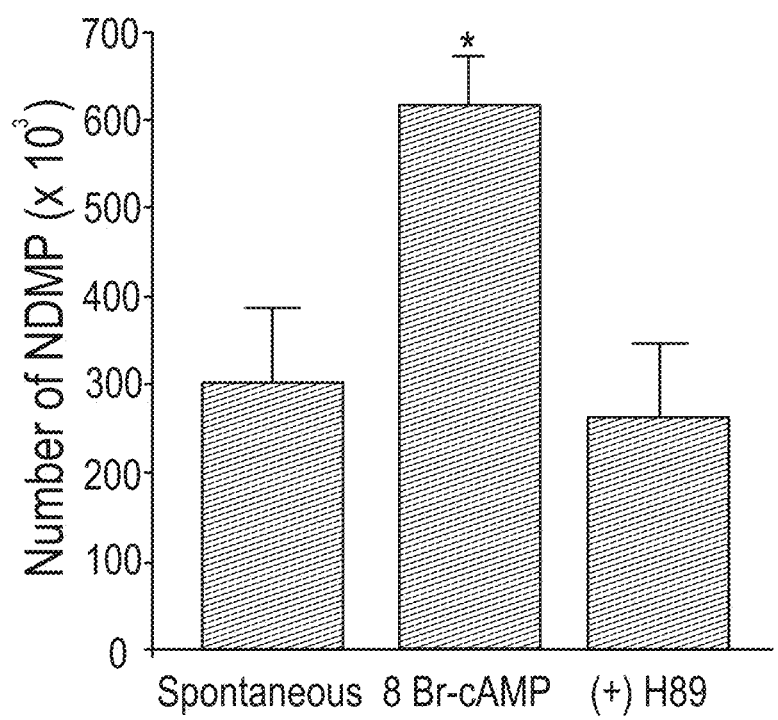
Figure 19:
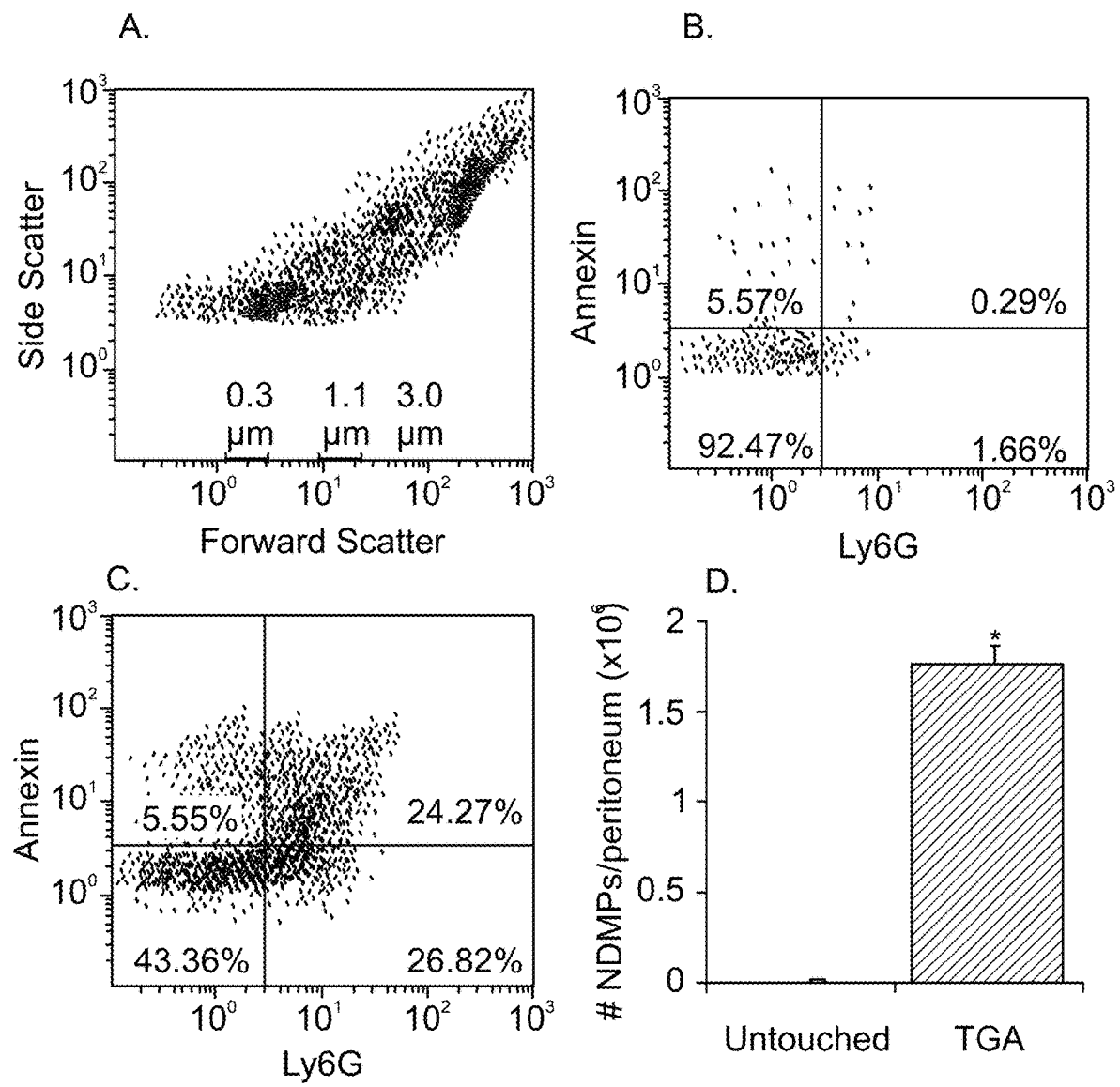
Figure 20:
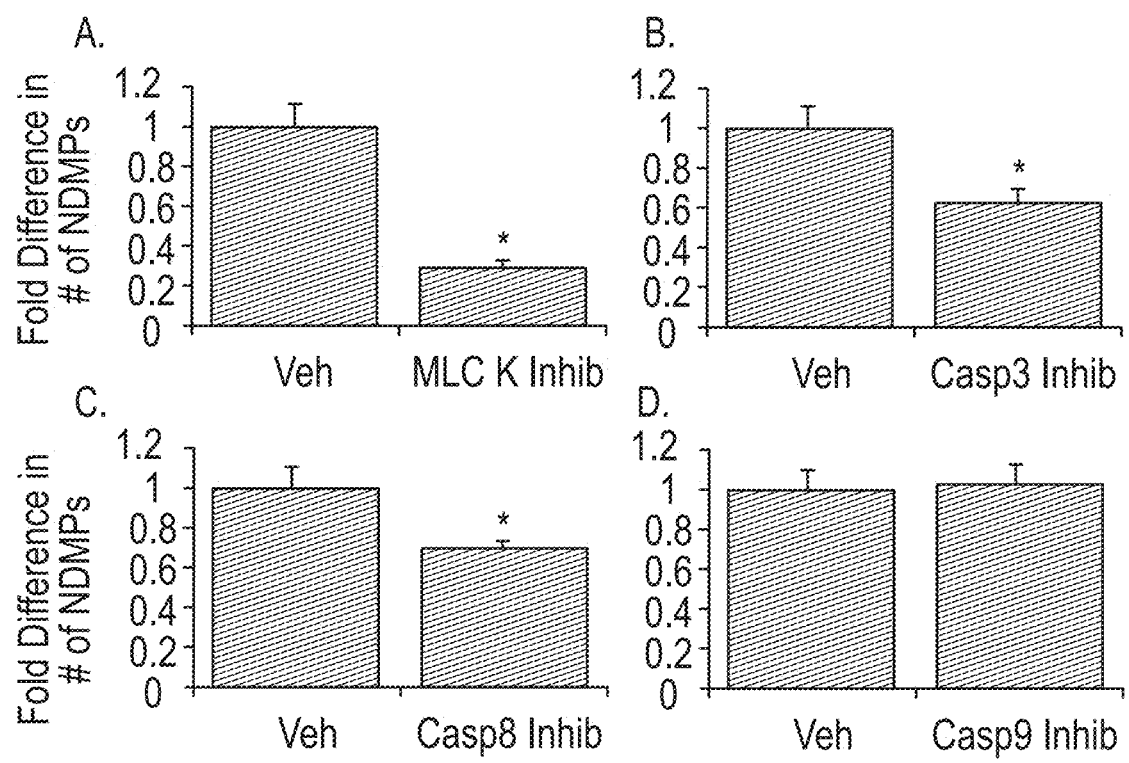
Figure 21:
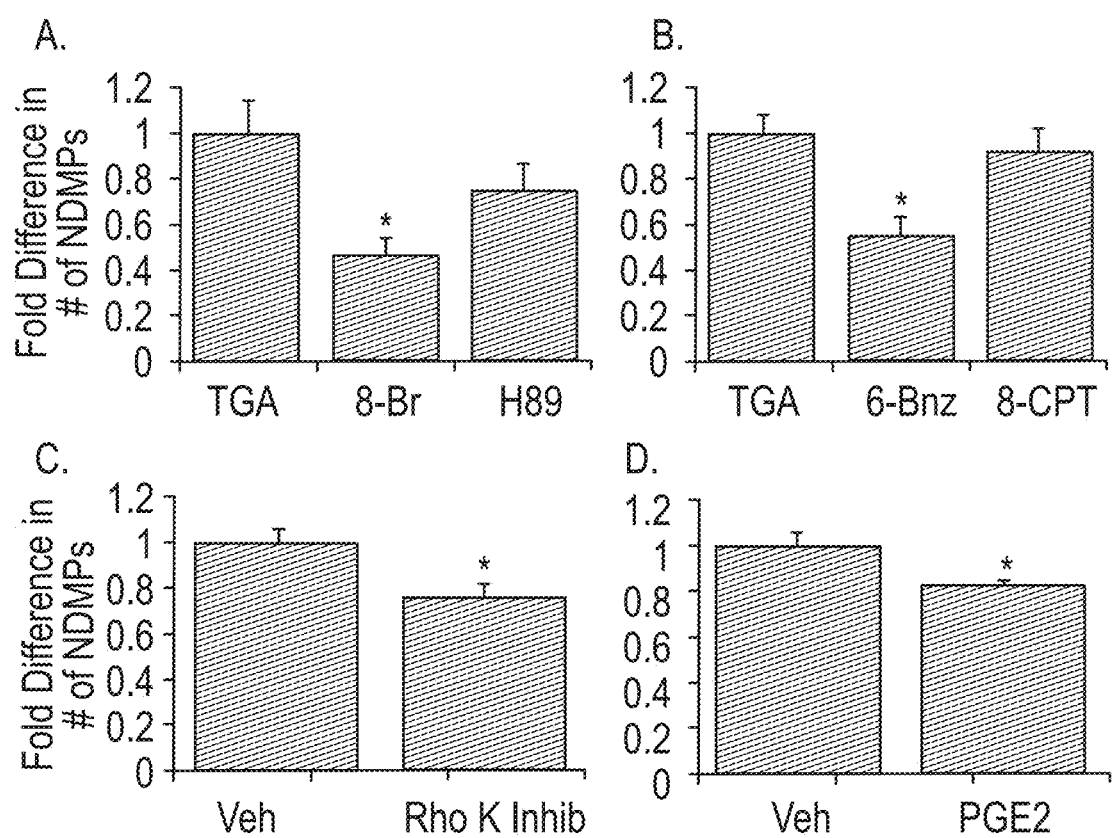

FIG. 11 is a graph of washes of peritoneal CLP-derived microparticles isolated and repeatedly washed using endotoxin-free saline with respect to endotoxin/MP, wherein each wash diluted the supernatant associated with MP pellet (~2,000-fold) and MPs were quantified by flow cytometry using True Count beads and endotoxin was determined by Limulus Amoebocyte Lysate assay;

FIG. 12 is a graph of survival (H) of mice undergoing CLP intraperitoneally injected with endotoxin-free saline vehicle or a bolus of MPs in saline (65,000) isolated previously TGA-treated mice, wherein sample size=16, p=0.025 as determined by log-rank (Mantel-Cox) test;

FIG. 13 is (A) a graphic representation of microparticles isolated from septic mice analyzed for PS expression; (B) CFSE-labeled MPs incubated with macrophages for 3 H and phagocytosis determined by AMNIS; and (C) CFSE-labeled MPs incubated with macrophages for 3 H and phagocytosis determined by flow cytometry;

FIG. 14 is a bar graph of (A) peritoneal cells from mice intraperitoneally injected with TGA-derived microparticles or vehicles at the time of CLP evaluated for phagocytosis by flow cytometry, n=10/group; and (B) viable bacteria from the blood of mice intraperitoneally injected with TGA-derived microparticles or vehicles at the time of CLP quantified by flow cytometry, n=6 and p=0.1 as determined by Student T test;

FIG. 15 is a bar graph of peritoneal non-naïve T cells ($CD62L^{low}$) from mice intraperitoneally injected with TGA-derived NDMPs or vehicle for 24 H (A) quantified for CD44 expression; and (B) analyzed for CD44 expression, wherein sample size=5, *, p<0.05 compared to vehicle injected;

FIG. 16 is a bar graph of (A) peritoneal macrophages from naïve mice injected intraperitoneally with TGA-derived microparticles (65,000) or vehicle for 24 H evaluated for CD11b by flow cytometry; (B) peritoneal macrophages from naïve mice injected intraperitoneally with TGA-derived microparticles (65,000) or vehicle for 24 H evaluated for MHC II surface expression by flow cytometry; and (C) Ex vivo peritoneal maacrophages assessed for intracellular TNF-α production after in vitro activation by LPS (100 ng/mL), wherein n=5, *, p<0.05 as determined by Student T test;

FIG. 17 is a graphical representation of (A) latex beads of a predetermined size were used to set the forward and side scatter voltages to best distinguish particles ranging from 0.3 to 1.0 μM; (B) peritoneal cells isolated from septic mice 24 H after CLP incubated with PBS (100 ng/mL) for 24 H; and (C) peritoneal cells isolated from septic mice 24 H after CLP incubated with LPS (100 ng/mL) for 24 H, wherein samples were analyzed using LSR II flow cytometer and FACS Diva software;

FIG. 18 is a bar graph of peritoneal cells isolated from mice 24 H after CLP incubated with saline vehicle, 8-Br cAMP (10 μM) or H89 PKA inhibitor (20 μM) for 24 H with respect to NDMPs ($\times 10^3$), wherein the peritoneal cells were enumerated and characterized by flow cytometry, n=7/group, *, p<0.05 compared to spontaneous, or compared to spontaneous and H89;

FIG. 19 is a graphical representation of microparticles derived from peritoneal cells from C57BL/6 mice intraperitoneally injected with 3% TGA (1 mL) or vehicle and peritoneal lavage performed 24 H later, wherein: (A) microparticle populations identified by gating on latex beads sized between 0.3-1.1 μm; (B) NDMPs identified by annexin and Ly6G surface staining in untouched mouse; (C) NDMPs identified by annexin and Ly6G surface staining in a TGA-treated mouse; and (D) enumeration of microparticles in the peritoneum of TGA treated mice, wherein NDMPs in untreated mice=9875;

FIG. 20 is a bar graph of peritoneal cells collected after 24 H with TGA treatment with respect to fold difference in the number of NDMPs and cultured with the following inhibitors: (A) Myosin Light Chain Kinase Inhibitor ML7 (250 μM); (B) Caspase 3 Inhibitor Z-VAD-FMK (200 μM); (C) Caspase 8 Inhibitor Z-IETD-FMK (30 μM); and (D) Caspase 9 Inhibitor Z-LEHD-FMK (30 μM) enumerated and characterized by flow cytometry, wherein data are expressed as means±SEM, p<0.05 as compared to control; and FIG. 21 is a bar graph of peritoneal cells collected after 24 H TGA treatment with respect to fold difference in the number of NDMPs and cultured with the following agonists and inhibitors: (A) cAMP analogue 8-Br-cAMP (100 μM) and PKA inhibitor H-89 (20 μM); (C) Rho Kinase Inhibitor Y27632 (30 μM); and (D) Prostaglandin E2 (1 μM).

Figure 22:
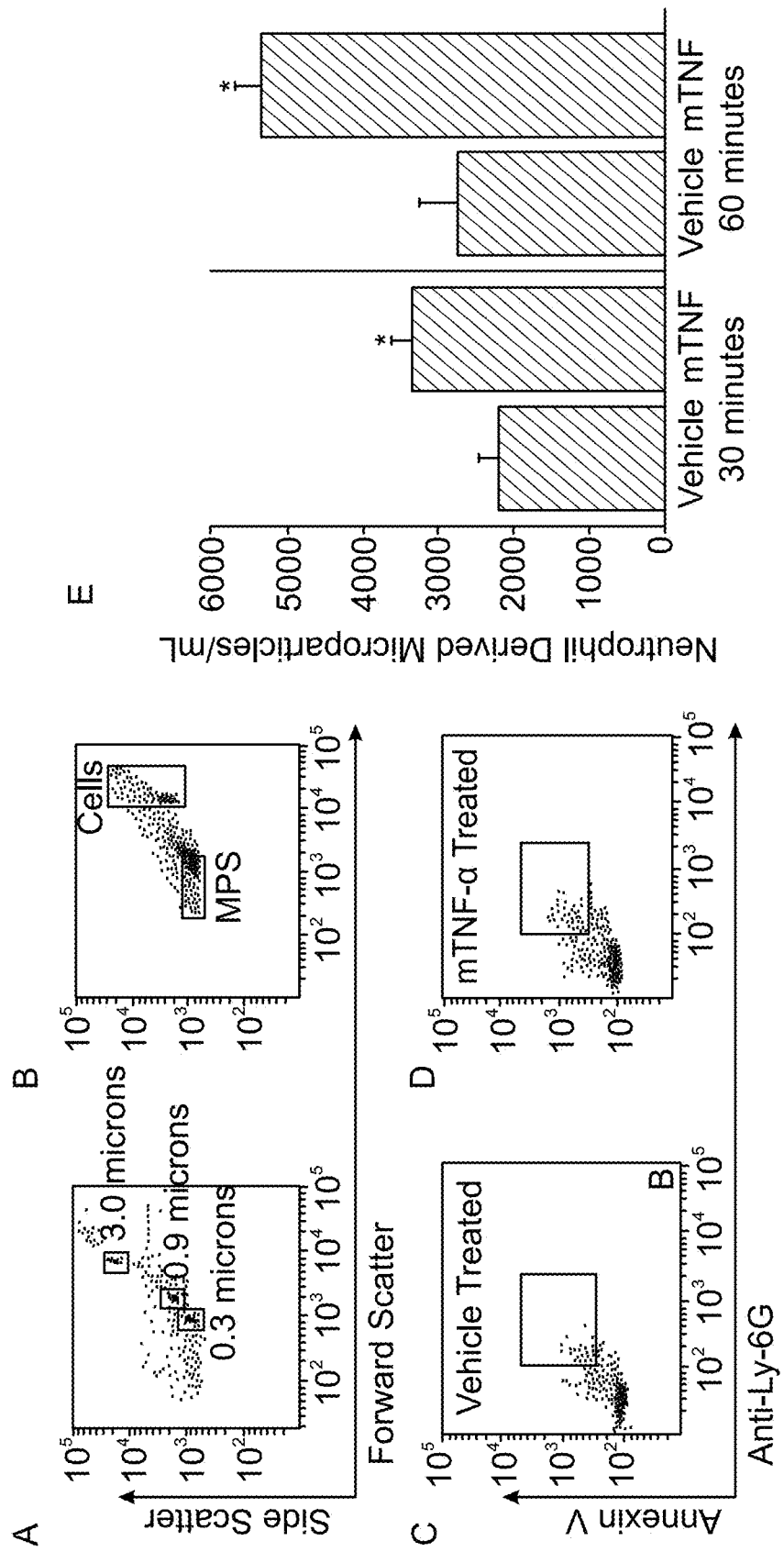

FIG. 22 is a graphical representation of data demonstrating that TNF-α treatment in vitro increases NDMP levels. Neutrophils were isolated from bone marrow as described in the examples: (A) Sizing for the microparticle populations was based upon latex beads sized between 0.5 and 3.0 μm. (B) Representative flow cytometric analysis of the forward and side scatter of a cell microparticle mixture obtained from culture. MP (microparticle gate) (C) Representative flow cytometric analysis using anti-Ly-6G (mouse neutrophil specific marker) and Annexin V (apoptosis marker) treated with vehicle. (D) with 25 ng/mL rmTNF-α. (EP Neutrophils were treated with rmTNF-α (25 ng/mL) and enumerated by flow cytometry at the indicated times. (Data are expressed as the mean±the SEM. The significance was determined using Student T-test at respective time points. *p<0.05 compared vehicle. MP—microparticles, mTNF—murine tumor necrosis factor.)

Figure 23:
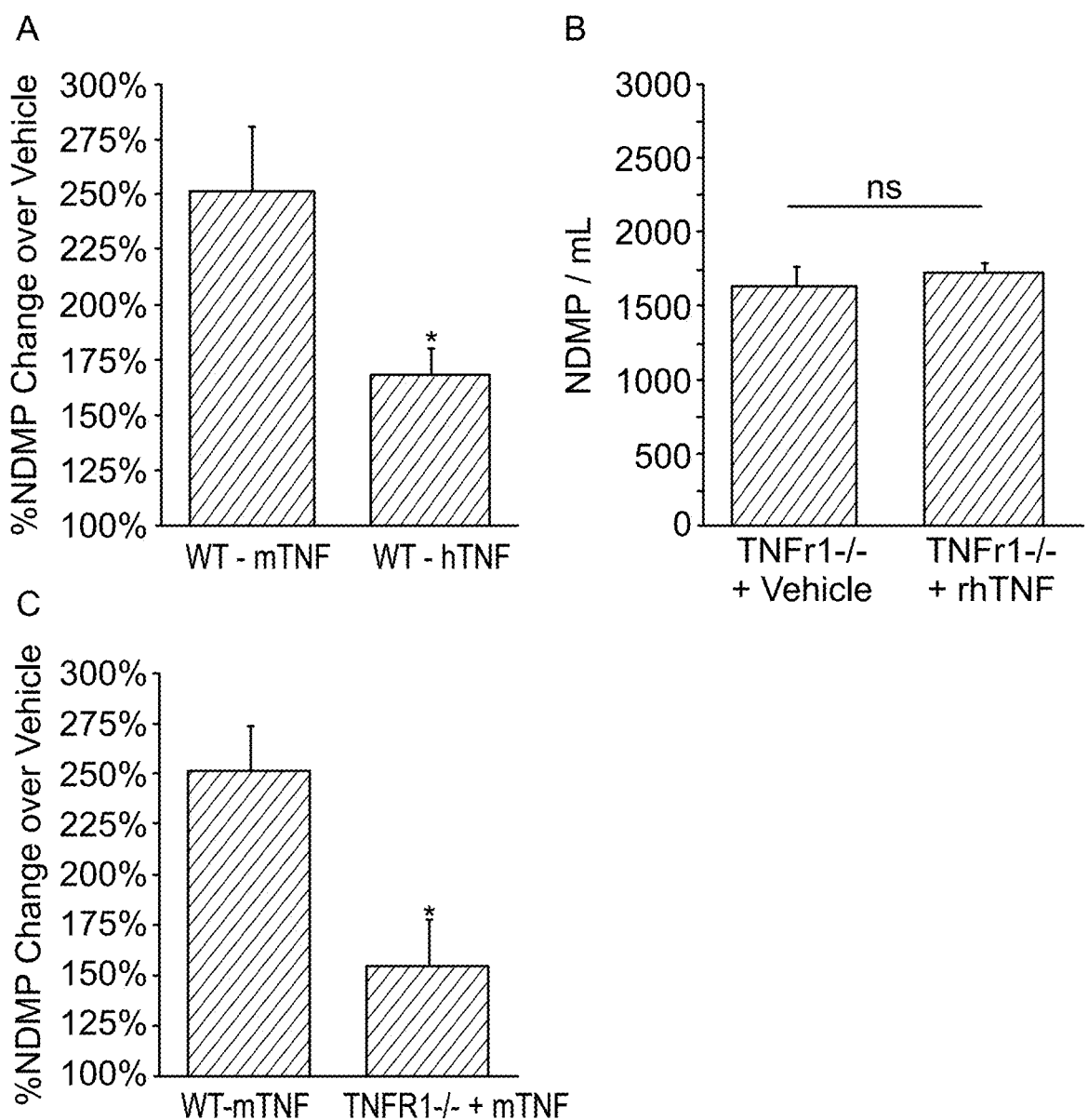

FIG. 23 is a bar graph showing that the production of NDMPs is additive upon TNFr1 and TNFr2 activation. Mouse neutrophils were isolated from bone marrow and cultured in vitro as described in the examples. (A) Neutrophils from WT mice were treated with either 25 ng/mL of rmTNF-α (activates both TNFr1 and TNFr2) or 25 ng/mL of rhTNF-α (TNFr1 specific). After 1 h, NDMPs were analyzed by flow cytometry. The sample size=12 mice. (B) Neutrophils from TNFr1−/− mice treated with vehicle or 25 ng/mL of rhTNF-α. After 1 h, NDMPs were analyzed by flow cytometry. The sample size=8 mice. (C) Neutrophils from either WT mice or TNFr1-/0 mice were treated with 25 ng/mL of rmTNF-α. After 1 h, NDMPs were analyzed by flow cytometry. (All data are expressed in fold increase above vehicle and as means±SEM. The significance was determined using ANOVA analysis and Tukey post hoc test. *p<0.05 compared vehicle.)

Figure 24:
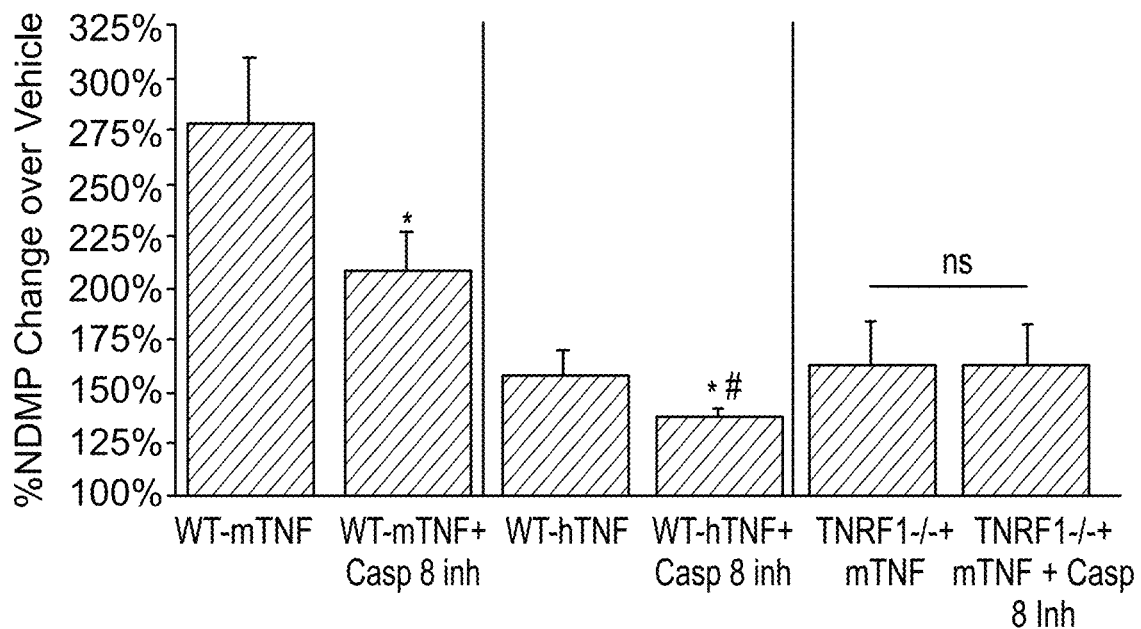

FIG. 24 is a bar graph showing that TNFr1-specific generation of NDMPs is partially dependent upon caspase-8 activation. Mouse neutrophils were isolated from bone marrow from either WT or TNFr1−/− mice and cultured in vitro as described in the examples. Neutrophils were treated as indicated with 25 ng/mL rmTNF-α or 25 ng/ml rhTNF-α, or ±30 μM of Caspase-8 inhibitor (Z-IETD-FMK). After 1 h, NDMPs were enumerated by flow cytometry. (The data are expressed in fold increase above vehicle and as means±SEM. The significance was determined using ANOVA analysis and Tukey post hoc test. *p<0.05 compared rm/rhTNF-α alone. # p<0.05 compared to vehicle.)

Figure 25:
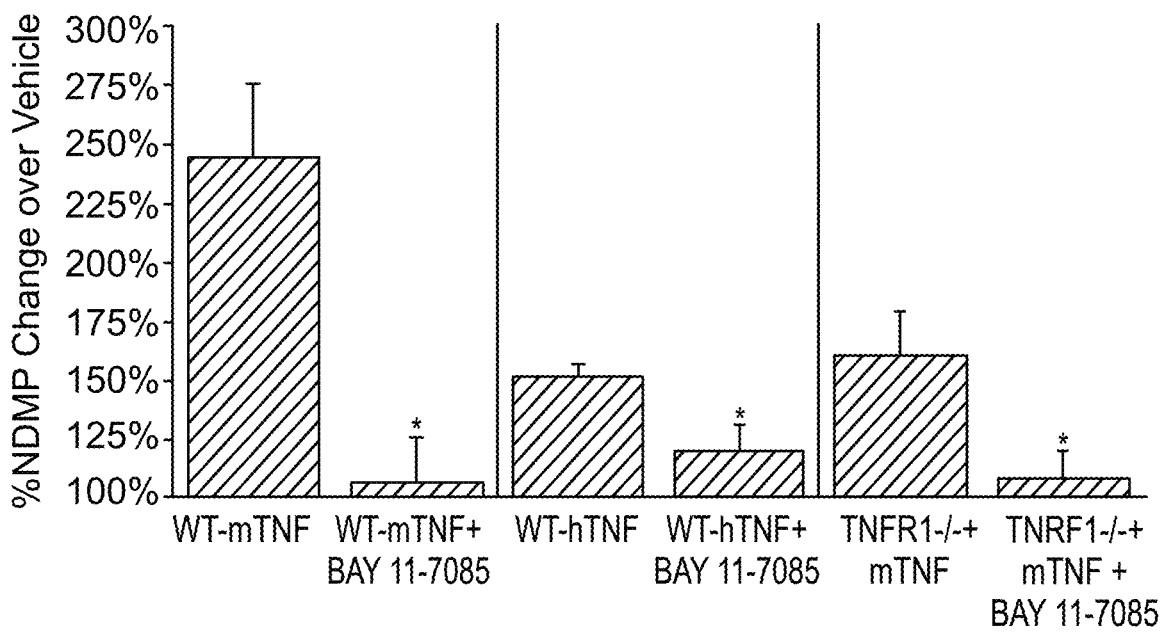

FIG. 25 is a bar graph showing that treatment with an NF-κB inhibitor decreases NDMP production induced by either TNFr1 or TNFr2 activation. Mouse neutrophils were isolated from bone marrow of WT or TNFr1−/− mice and cultured in vitro as described in the examples. Neutrophils were treated as indicated with 25 ng/mL tmTNF-α or 25 ng/mL rhTNF-α±20 μM of NF-κB inhibitor (BAY11-7085). After 1 h, NDMPs were enumerated by flow cytometry. (Data are expressed in fold increase above vehicle and as means±SEM. The significance was determined using ANOVA analysis and Tukey post hoc test. *$p<0.05$ compared to rh/rmTNF-α treatment samples.)

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

The following terms are used in the present application:

As used herein, the terms "diagnosing", "diagnosed", and "diagnose" refer to determining the presence and/or absence of a disease or condition based upon an evaluation of physical signs, symptoms, history, laboratory test results, and/or procedures. Specifically, in the context of pneumonia and/or sepsis, diagnosing refers to determining the presence or absence of a disease or condition based upon an evaluation of the level of NDMPs.

As used herein, the term "positive diagnosis" refers to a determination of the presence of a disease or condition based upon an evaluation of physical signs, symptoms, history, laboratory test results, and/or procedures. In the context of pneumonia and/or sepsis, a positive diagnosis refers to a determination of the presence of pneumonia and/or sepsis based upon an evaluation of the level of NDMPs.

As used herein, the term "negative diagnosis" refers to a determination of the absence of a disease or condition based upon an evaluation of physical signs, symptoms, history, laboratory test results, and/or procedures. In the context of pneumonia and/or sepsis, a negative diagnosis refers to a determination of the absence of pneumonia and/or sepsis based upon an evaluation of the level of NDMPs.

In the context of NDMPs, the term "elevated level" refers to the level of NDMPs in a biological sample which is greater than a cutoff value of NDMPs. For example, in the context of pneumonia, an elevated level of NDMPs in blood plasma may be from about 750 NDMPs/μL to about 2000 NDMPs/μL, or from about 1000 NDMPs/μL to about 1500 NDMPs/μL, or about 1200 NDMPs/μL. In one embodiment, the elevation of the level of NDMPs in the biological sample is statistically significant.

As used herein, the term "cutoff value" refers to a threshold value which distinguishes patients and/or subjects suffering from a disease or condition from patients and/or subjects who are not suffering from the disease or condition. In the context of pneumonia and/or sepsis, an elevated level of NDMPs is greater than the cutoff value and a non-elevated level of NDMPs is less than or equal to the cutoff value. For example, specifically regarding pneumonia, the cutoff value of NDMPs may be about 500 NDMPs/μL.

As used herein, the terms "baseline level" and/or "baseline concentration" refer to the level and/or concentration of NDMPs in a biological sample from a patient and/or subject prior to administration of a treatment and/or to the level of NDMPs in a biological sample from a patient and/or subject who is not suffering from pneumonia and/or sepsis.

Embodiments of diagnosing and treating pneumonia and/or sepsis and modulation of an immune response will now be described.

I. Diagnosing Pneumonia and/or Sepsis

Methods of diagnosing pneumonia and/or sepsis in a patient are disclosed. In one embodiment, a method for diagnosing pneumonia in a patient is disclosed. The method may include: (a) obtaining a biological sample from the patient; (b) determining a level of NDMPs in the biological sample; (c) comparing the level of NDMPs determined in step (b) with a cutoff value of NDMPs; and (d) diagnosing pneumonia in the patient, wherein an elevated level of NDMPs as compared to the cutoff value correlates to a positive diagnosis of pneumonia in the patient.

In one embodiment, the method of diagnosing pneumonia in the patient includes obtaining a biological sample from the patient in step (a). In one particular embodiment, the biological sample is bronchoalveolar lavage fluid (hereinafter, "BALf"). Such fluid may be obtained via bronchoalveolar lavage which may be performed according to any bronchoalveolar lavage methods known in the field. For example, bronchoalveolar lavage may be performed in accordance with Intensive Care Unit clinical practice guidelines. In one embodiment, such bronchoalveolar lavage includes: (i) passing a bronchoscope through the mouth and/or nose into the lung(s); (ii) depositing (e.g., squirting) fluid suitable for such procedure into at least a portion of the lung(s); and (iii) recollecting the deposited fluid from the lung(s) for examination. In one particular embodiment, the fluid suitable for such procedure is sterile. In a further embodiment, the fluid suitable for such procedure is a sterile saline solution (e.g., sterile phosphate-buffered saline). In one particular embodiment, the patient is human.

In another embodiment, the method of diagnosing pneumonia in the patient includes determining a level of NDMPs in the biological sample in step (b). In one embodiment, determining the level of NDMPs in the biological sample includes: (i) optionally isolating MPs via differential centrifugation; and (b) detecting and/or quantifying the NDMPs in the MPs via flow cytometry. Isolation of the MPs from the biological sample via differential centrifugation may be accomplished by performing differential centrifugation according to any methods known in the field. The differential centrifugation may be performed under conditions suitable for isolating MPs as may be known in the field.

For example, in one embodiment, performing differential centrifugation includes: performing a first centrifugation of the biological sample at a first acceleration, performing a second centrifugation of a first supernatent formed from the first centrifugation at a second acceleration, and performing a third centrifugation of a second supernatent formed form the second centrifugation at a third acceleration. In one embodiment, the first acceleration is from about 200 g to 1,000 g, or from about 300 g to about 900 g, or from about 400 g to about 800 g, or from about 500 g to about 700 g, or from about 450 g to about 600 g, or about 450 g. In another embodiment, the second acceleration is from about 9,500 g to about 10,500 g, or from about 9,600 g to about 10,400 g, or from about 9,700 g to about 10,300 g, or from about 9,800 g to about 10,200 g, or from about 9,900 g to about 10,100 g, or from about 9,950 g to about 10,000 g, or about 9,900 g. In yet another embodiment, the third acceleration is from about 16,500 g to about 17,500 g, or from about 16,600 g to about 17,400 g, or from about 16,700 g to about 17,300 g, or from about 16,800 g to about 17,200 g, or from about 16,900 g to about 17,100 g, or from about 16,950 g to about 17,000 g, or about 17,000 g. In one particular embodiment, the first acceleration is about 450 g, the second acceleration is about 9,900 g, and the third acceleration is about 17,000 g.

The first centrifugation may be performed for a first time period, the second centrifugation may be performed for a second time period, and the third centrifugation may be performed for a third time period. For example, in one embodiment, the first time period is from about 1 minutes to about 12 minutes, or from about 2 minutes to about 11 minutes, or from about 3 minutes to about 10 minutes, or from about 4 minutes to about 9 minutes, or from about 5 minutes to about 8 minutes, or from about 6 minutes to about 7 minutes, or about 10 minutes. In another embodiment, the second time period is from about 1 minutes to about 12 minutes, or from about 2 minutes to about 11 minutes, or from about 3 minutes to about 10 minutes, or from about 4 minutes to about 9 minutes, or from about 5 minutes to about 8 minutes, or from about 6 minutes to about 7 minutes, or about 5 minutes. In yet another embodiment, the third time period is from about 12 minutes to about 26 minutes, or from about 13 minutes to about 25 minutes, or from about 14 minutes to about 24 minutes, or from about 15 minutes to about 23 minutes, or from about 16 minutes to about 22 minutes, or from about 17 minutes to about 21, or from about 18 minutes to about 20 minutes, or about 19 minutes, or about 20 minutes. In one embodiment, the first centrifugation forms a first pellet and a first supernatent, the second centrifugation forms a second pellet and a second supernatent, and the third centrifugation forms a third pellet and a third supernatent. The first pellet may include cells from the biological sample, the second pellet may include platelets from the biological sample, and the third pellet may include MPs from the biological sample.

Detection and/or quantification of the NDMPs may be accomplished via flow cytometry which may be performed according to any methods known in the field. In one particular embodiment, detection and/or quantification of the NDMPs is accomplished via fluorescence-activated cell sorting according to methods known in the field. The flow cytometry and/or fluorescence-activated cell sorting may be performed at conditions suitable for detecting and/or quantifying the NDMPs. For example, in one embodiment, performing fluorescence-activated cell sorting includes: contacting the biological sample with reagents for detection and/or quantification of NDMPs, exposing the biological sample to light of a single wavelength, and receiving scattered light and/or fluorescence emitted therefrom.

In one embodiment, the biological sample is contacted with reagents for detection and/or quantification of NDMPs. Suitable techniques for contacting the biological sample with reagents for detection and/or quantification of NDMPs include dispersing, dissolving, diffusing, or otherwise mixing the biological sample and the reagents for detection and/or quantification of NDMPS. In one particular embodiment, the biological sample contacted with the reagents for detection and/or quantification of NDMPs are dispersed, dissolved, diffused, mixed, or otherwise provided in a fluid. In one embodiment, the reagents for detection and/or quantification of NDMPs include at least one antibody having specific binding affinity to NDMPs in the biological sample. Such antibody may also have specific binding affinity to neutrophils. In one particular embodiment, the antibody having specific binding affinity to NDMPs is anti-human CD66b.

In another embodiment, the antibody having specific binding affinity to NDMPs is fluorescently labeled. The antibody having specific binding affinity to NDMPs may be fluorescently labeled with a fluorophore. Examples of fluorophores which may be suitable for fluorescent labeling of the antibody include fluorescent proteins, non-protein organic fluorophores, dye families, and combinations thereof. With regard to fluorescent proteins, suitable fluorophores may include green fluorescent protein, yellow fluorescent protein, red fluorescent proteins, fusion proteins includes such fluorescent proteins, and combinations thereof. With regard to non-protein organic fluorophores, suitable fluorophores may include xanthene derivatives (e.g., fluorescein, rhodamine, Oregon green, eosin, and Texas red), cyanine derivatives (e.g., cyanine, indocarbocyanine, oxacarbocyanine, thiacarbocyanine, and merocyanine), napthalene derivatives (e.g., dansyl and prodan derivatives), coumarin derivatives, oxadiazole derivatives (e.g., pryidyloxazole, nitrobenzoxadiazole, and benzoxadiazole), pyrene derivatives (e.g., cascade blue), oxazine derivatives (e.g., Nile red, Nile blue, cresyl violet, and oxazine 170), acridine derivatives (e.g., proflavin, acridine orange, and acridine yellow), arylmethine derivatives (e.g., auramine, crystal violet, and malachite green), tetrapyrrole derivatives (e.g., porphin, phtalocyanine, and bilirubin), and combinations thereof. In one particular embodiment, the antibody having specific binding affinity to NDMPs is fluorescently labeled with fluorescein isothiocyanate. In a further embodiment, the antibody having specific binding affinity to NDMPs is fluorescein isothiocyanate anti-human CD66b.

In one embodiment, the biological sample is exposed to light of a single wavelength. In a further embodiment, the biological sample is exposed to light of a single wavelength after contacting the biological sample with the reagents for detection and/or quantification of NDMPs. Suitable techniques for exposing the biological sample contacted with the reagents for detection and/or quantification of NDMPs include directing a beam of light of a single wavelength (e.g., laser(s) light(s)) onto a stream of fluid, wherein the fluid provides the biological sample and the reagents for detection and/or quantification of NDMPs. Such exposure scatters the light and/or excites fluorescent chemicals in the biological sample such that the fluorescent chemicals emit fluorescence. The fluorescent chemicals may be provided within, attached to, adhered to, associated with, and/or contacted with the biological sample. In one particular embodiment, the fluorescent chemicals are contacted with the biological sample via a fluorescently labeled antibody having specific binding affinity to NDMPs. For example, the fluorescent chemicals may be contacted with the viological sample via a fluorescein isothiocyanate labeled anti-human CD66b (e.g., fluorescein isothiocyanate anti-human CD66b).

In one embodiment, the light scattered and/or fluorescence emitted by the fluorescent chemicals as previously described are received. Suitable techniques for receiving the scattered light and/or fluorescence emitted by the fluorescent chemicals as previously described include aiming detector (s) at a point where fluid containing the biological sample and reagents for quantification and/or detection of NDMPs pass through the beam of light of a single wavelength.

In another embodiment, the method for diagnosing pneumonia includes comparing the level of NDMPs determined in step (b) with a cutoff value of NDMPs in step (c).

In yet another embodiment, the method for diagnosing pneumonia in the patient includes diagnosing pneumonia in the patient in step (d), wherein an elevated level of NDMPs as compared to the cutoff value correlates to a positive diagnosis of pneumonia in the patient. In one particular embodiment, the elevated level of NDMPs is from about 750 NDMPs/μL to about 2,500 NDMPs/μL, or from about 1,000 NDMPs/μL to about 2,000 NDMPs/μL, or from about 1,250 NDMPs/μL to about 1,750 NDMPs/μL, or about 1,500 NDMPs/μL. In another embodiment, a non-elevated level of NDMPs as compared to the cutoff value correlates to a negative diagnosis of pneumonia.

In a further embodiment, the method for diagnosing pneumonia also includes determining a pathogenic source of the pneumonia wherein the determined level of NDMPs is elevated. In one embodiment, the pathogenic source of the pneumonia may be gram positive bacteria wherein the determined level of NDMPs is elevated relative to a threshold value. In another embodiment, the pathogenic source of the pneumonia may be gram negative bacteria wherein the determined level of NDMPs is non-elevated as compared to the threshold value. In one particular embodiment, the threshold value is greater than the cutoff value.

In another embodiment, a method for diagnosing sepsis is disclosed. In one embodiment, the method includes (a) obtaining a biological sample from the patient; (b) determining a level of NDMPs in the biological sample; (c) comparing the level of NDMPs determined in step (b) with a cutoff value of NDMPs; and (d) diagnosing sepsis in the patient, wherein an elevated level of NDMPs as compared to the cutoff value correlates to a positive diagnosis of sepsis in the patient.

In one embodiment, the method of diagnosing sepsis in the patient includes obtaining a biological sample from the patient in step (a). In one particular embodiment, the biological sample is obtained from infectious foci in the patient. For example, in one embodiment, the biological sample is obtained from the abdomen. More particularly, the biological sample may be abdominal irrigation fluid and/or peritoneal waste fluid. Such fluid may be obtained via abdominal irrigation which may be performed according to any abdominal irrigation methods known in the field. In one particular embodiment, the patient is human.

In another embodiment, the method of diagnosing sepsis in the patient includes determining a level of NDMPs in the biological sample in step (b). In one embodiment, determining the level of NDMPs in the biological sample includes: (i) optionally isolating MPs via differential centrifugation; and (b) detecting and/or quantifying the NDMPs in the MPs via flow cytometry. Isolation of the MPs from the biological sample via differential centrifugation is as previously described with regard to diagnosing pneumonia. Detection and/or quantification of the NDMPs may be accomplished via flow cytometry which may be performed according to any methods known in the field. Such detection and/or quantification is also as previously described with regard to diagnosing pneumonia.

In another embodiment, the method for diagnosing sepsis includes comparing the level of NDMPs determined in step (b) with a cutoff value of NDMPs in step (c).

In yet another embodiment, the method for diagnosing sepsis in the patient includes diagnosing sepsis in the patient in step (d), wherein an elevated level of NDMPs as compared to the cutoff value correlates to a positive diagnosis of sepsis in the patient. In another embodiment, a non-elevated level of NDMPs as compared to the cutoff value correlates to a negative diagnosis of sepsis.

Embodiments of methods of diagnosing pneumonia and/or sepsis have now been described in detail. Further embodiments directed to assessing pneumonia and/or sepsis will now be described.

II. Assessing Pneumonia and/or Sepsis

In another embodiment, in vitro methods for assessing pneumonia and/or sepsis in a patient (or subject) are disclosed. In one embodiment, an in vitro method for assessing pneumonia in a patient is disclosed. The method includes (a) contacting at least a portion of a biological sample from the patient with reagents for detection and/or quantification of NDMPs. The method also includes (b) determining a level of NDMPs based on the contacting in step (a). Additionally, the method includes (c) assessing as indicating pneumonia in the patient if the determined level of NDMPs is elevated relative to a cutoff value of the NDMPs.

In one embodiment, the method for assessing pneumonia includes contacting at least a portion of the biological sample from the patient with reagents for detection and/or quantification of NDMPs in step (a). The biological sample, patient, and reagents for detection and/or quantification are as previously described. The biological sample may be contacted with the reagents for detection and/or quantification of NDMPs via dispersing, dissolving, diffusing, or otherwise mixing the biological sample and the reagents for detection and/or quantification of NDMPS. In one embodiment, MPs are isolated from the biological sample prior to the contacting in step (a) and/or prior to determining the level of NDMPs in step (b). The MPs may be isolated from the biological sample via techniques known in the field. For example, in one embodiment, the MPs are isolated from the biological sample via differential centrifugation as previously described. In a further embodiment, the at least a portion of the biological sample consists essentially of MPs isolated via differential centrifugation.

In another embodiment, the method for assessing pneumonia includes (b) determining a level of NDMPs based on the contacting in step (a). Determining the level of NDMPs based on the contacting in step (a) may be performed as previously described (e.g., via flow cytometry and/or fluorescence-activated cell sorting).

In another embodiment, the method for assessing pneumonia includes (c) assessing as indicating pneumonia in the patient if the determined level of NDMPs is elevated relative to a cutoff value of the NDMPs. In this embodiment, an elevated level of NDMPs and the cutoff value of the NDMPs are as previously described.

In a further embodiment, the method for assessing pneumonia also includes determining a pathogenic source of the pneumonia wherein the determined level of NDMPs is elevated. In one embodiment, the pathogenic source of the pneumonia may be gram positive bacteria wherein the determined level of NDMPs is elevated relative to a threshold value. In another embodiment, the pathogenic source of the pneumonia may be gram negative bacteria wherein the determined level of NDMPs is non-elevated as compared to the threshold value. The threshold value is as previously described.

In another embodiment, an in vitro method for assessing sepsis in a patient is disclosed. The method includes (a) contacting at least a portion of a biological sample from the patient with reagents for detection and/or quantification of NDMPs. The method also includes (b) determining a level of NDMPs based on the contacting in step (a). Additionally, the method includes (c) assessing as indicating sepsis in the patient if the determined level of NDMPs is elevated relative to a cutoff value of the NDMPs.

In one embodiment, the method for assessing sepsis includes contacting at least a portion of the biological sample from the patient with reagents for detection and/or quantification of NDMPs in step (a). The biological sample, patient, and reagents for detection and/or quantification are as previously described. The biological sample may be contacted with the reagents for detection and/or quantification of NDMPs via dispersing, dissolving, diffusing, or otherwise mixing the biological sample and the reagents for detection and/or quantification of NDMPS. In one embodiment, MPs are isolated from the biological sample prior to the contacting in step (a) and/or prior to determining the level of NDMPs in step (b). The MPs may be isolated from the biological sample as previously described. In a further embodiment, the at least a portion of the biological sample consists essentially of MPs isolated via differential centrifugation.

In another embodiment, the method for assessing sepsis includes (b) determining a level of NDMPs based on the contacting in step (a). Determining the level of NDMPs based on the contacting in step (a) may be performed as previously described (e.g., via flow cytometry and/or fluorescence-activated cell sorting).

In another embodiment, the method for assessing sepsis includes (c) assessing as indicating pneumonia in the patient if the determined level of NDMPs is elevated relative to a cutoff value of the NDMPs. In this embodiment, an elevated level of NDMPs and the cutoff value of the NDMPs are as previously described.

Embodiments of methods of assessing pneumonia and/or sepsis have now been described in detail. Further embodiments directed to managing treatment of pneumonia and/or sepsis will now be described.

III. Managing Treatment of Pneumonia and/or Sepsis

In another embodiment, methods for managing treatment of pneumonia and/or sepsis are disclosed. In one embodiment, a method for managing treatment of a patient (or subject) suspected of having pneumonia is disclosed. The method includes (a) assessing pneumonia in vitro in the patient by calculating a concentration of NDMPs, wherein an elevated concentration of NDMPs relative to a cutoff value of NDMPs is indicative of pneumonia. The method also includes (b) treating the patient for pneumonia where pneumonia is indicated in step (a), wherein the calculated concentration of NDMPs is elevated. Additionally, the method includes (c) placing the patient under active surveillance where pneumonia is not indicated in step (a), wherein the calculated concentration of NDMPs is not elevated.

In one embodiment, the method for managing treatment of pneumonia includes (a) assessing pneumonia in vitro in the patient by calculating a concentration of NDMPs wherein an elevated concentration of NDMPs relative to a cutoff value of NDMPs is indicative of pneumonia. The concentration of NDMPs may be calculated as previously described with regard to determining a level of NDMPs. Additionally, an elevated concentration of NDMPs and a cutoff value of NDMPs are as previously described.

In one embodiment, the method for managing treatment of pneumonia also includes (b) treating the patient for pneumonia where pneumonia is indicated in step (a), wherein the calculated concentration of NDMPs is elevated. In one embodiment, treatment of the patient may include administration of antibiotics, antivirals, fluids, and combinations thereof. Any suitable antibiotics and/or antivirals may be administered as treatment for pneumonia as are known in the field. For example, in one embodiment, the antibiotics are selected from the group consisting of: penicillins, cephalosporins, polymixins, rifamycins, lipiarmycins, quinolones, sulfonamides, amigoglycosides, macrolides, tetracyclines, cyclic lipopeptides, glycylcyclines, oxazolidinones, lipiarmycins, and combinations thereof. Specific examples of antibiotics may include amoxicillin, cefuroxime, ethryomycin, flucoxacillin, doxycycline, ciprofloxacin, rifampicin, clarithromycin, azithromycin, fluoroquinolones, cephalosporins, carbapenems, aminoglycosides, vancomycin, and combinations thereof. In another embodiment, the antivirals are neuramidase inhibitors. Specific examples of neuramidase inhibitors include oseltamivir, zanamivir, laninamivir, peramivir, and combinations thereof.

In a further embodiment, the method for managing treatment of pneumonia also includes determining a pathogenic source of the pneumonia wherein the determined level of NDMPs is elevated. In one embodiment, the pathogenic source of the pneumonia may be gram positive bacteria wherein the determined level of NDMPs is elevated relative to a threshold value. In another embodiment, the pathogenic source of the pneumonia may be gram negative bacteria wherein the determined level of NDMPs is non-elevated as compared to the threshold value. The threshold value is as previously described. Accordingly, the treatment of the patient may be adapted accordingly with regard to the pathogenic source. For example, in one embodiment, narrow spectrum antibiotics may be administered wherein the pathogenic source is identified as either gram positive or gram negative bacteria.

In another embodiment, a method of managing treatment in a patient (or subject) suffering from pneumonia is disclosed. The method includes (a) establishing a baseline concentration of NDMPs in a biological sample (e.g., bronchoalveolar lavage fluid sample) from the patient, (b) initiating treatment, and (c) serially monitoring a concentration of NDMPs in the patient during the treatment, wherein the treatment is managed to decrease the concentration of NDMPs in the patient.

In one embodiment, the method of managing treatment in a patient suffering from pneumonia includes (a) establishing a baseline concentration of NDMPs in a bronchoalveolar lavage fluid sample the patient. The baseline concentration of NDMPs is established as previously described with regard to determining a level of NDMPs and/or calculating a concentration of NDMPs. The patient and bronchoalveolar lavage fluid sample are as previously described. In one embodiment, the baseline concentration of NDMPs in the bronchoalveolar lavage fluid sample is elevated relative to the cutoff value. The cutoff value is as previously described.

In another embodiment, the method of managing treatment in a patient suffering from pneumonia also includes (b) initiating treatment. The treatment is as previously described. In another embodiment, the method of managing treatment in a patient suffering from pneumonia also includes (c) serially monitoring a concentration of NDMPs in the patient during treatment. The treatment is managed to decrease the concentration of NDMPs in the patient. The concentration of NDMPs in the patient is monitored as previously described with regard to determining a level of NDMPs and/or determining a concentration of NDMPs.

In a further embodiment, the method for managing treatment in a patient suffering from pneumonia also includes determining a pathogenic source of the pneumonia wherein the determined level of NDMPs is elevated. In one embodiment, the pathogenic source of the pneumonia may be gram positive bacteria wherein the determined level of NDMPs is elevated relative to a threshold value. In another embodiment, the pathogenic source of the pneumonia may be gram negative bacteria wherein the determined level of NDMPs is non-elevated relative to the threshold value. The threshold value is as previously described. Accordingly, the treatment of the patient may be adapted accordingly with regard to the pathogenic source. For example, in one embodiment, narrow spectrum antibiotics may be administered wherein the pathogenic source is identified as either gram positive or gram negative bacteria.

In another embodiment, a method for managing treatment of a patient (or subject) suspected of having sepsis is disclosed. The method includes (a) assessing sepsis in vitro in the patient by calculating a concentration of NDMPs, wherein an elevated concentration of NDMPs relative to a cutoff value of NDMPs is indicative of sepsis. The method also includes (b) treating the patient for sepsis where sepsis is indicated in step (a), wherein the calculated concentration of NDMPs is elevated. Additionally, the method includes (c) placing the patient under active surveillance where sepsis is not indicated in step (a), wherein the calculated concentration of NDMPs is not elevated.

In one embodiment, the method for managing treatment of sepsis includes (a) assessing sepsis in vitro in the patient by calculating a concentration of NDMPs wherein an elevated concentration of NDMPs relative to a cutoff value of NDMPs is indicative of sepsis. The concentration of NDMPs may be calculated as previously described with regard to determining a level of NDMPs. Additionally, an elevated concentration of NDMPs and a cutoff value of NDMPs are as previously described.

In one embodiment, the method for managing treatment of sepsis also includes (b) treating the patient for sepsis where sepsis is indicated in step (a), wherein the calculated concentration of NDMPs is elevated. In one embodiment, treatment of the patient may include administration of antibiotics, administration of intravenous fluids, surgical drainage, and providing support for organ dysfunction. With regard to antibiotics, any suitable antibiotics may be administered as treatment for sepsis as are known in the field. For example, in one embodiment, broad spectrum antibiotics maybe administered. In another embodiment, the antibiotics are selected from the group consisting of: penicillins, cephalosporins, polymixins, rifamycins, lipiarmycins, quinolones, sulfonamides, amigoglycosides, macrolides, tetracyclines, cyclic lipopeptides, glycylcyclines, oxazolidinones, lipiarmycins, and combinations thereof.

In another embodiment, a method of managing treatment in a patient (or subject) suffering from sepsis is disclosed. The method includes (a) establishing a baseline concentration of NDMPs in a biological sample (e.g., abdominal wash fluid) from the patient, (b) initiating treatment, and (c) serially monitoring a concentration of NDMPs in the patient during the treatment, wherein the treatment is managed to decrease the concentration of NDMPs in the patient.

In one embodiment, the method of managing treatment in a patient suffering from sepsis includes (a) establishing a baseline concentration of NDMPs in an abdominal wash fluid sample the patient. The baseline concentration of NDMPs is established as previously described with regard to determining a level of NDMPs and/or calculating a concentration of NDMPs. The patient and abdominal wash fluid sample are as previously described. In one embodiment, the baseline concentration of NDMPs in the abdominal wash fluid is elevated relative to the cutoff value. The cutoff value is as previously described.

In another embodiment, the method of managing treatment in a patient suffering from sepsis also includes (b) initiating treatment. The treatment is as previously described. In another embodiment, the method of managing treatment in a patient suffering from sepsis also includes (c) serially monitoring a concentration of NDMPs in the patient during treatment. The treatment is managed to decrease the concentration of NDMPs in the patient. The concentration of NDMPs in the patient is monitored as previously described with regard to determining a level of NDMPs and/or determining a concentration of NDMPs.

Further embodiments directed to kits for assessing pneumonia will now be described.

IV. Kit for Assessing Pneumonia and/or Sepsis

In another embodiment, kits for assessing pneumonia and/or sepsis are disclosed. In one particular embodiment, the kits are used to assess pneumonia and/or sepsis in patients. Generally, the kits may include reagents for detection and/or quantification of NDMPs. In one embodiment, the kits include reagents for detection and/or quantification of NDMPs in BALf. In another embodiment, the kits include reagents for detection and/or quantification of NDMPs in abdominal wash fluid. In one embodiment, the kits for assessing pneumonia and/or sepsis are differential centrifugation and/or flow cytometry kits which may be used to detect and/or quantify NDMPs. The reagents for detection and/or quantification of NDMPs are as previously described.

The kits may also include instructions to provide guidance on utilizing the kits for assessing pneumonia and/or sepsis. More particularly, the kits may include instructions to provide guidance on detecting and/or quantifying NDMPs. Such instructions may generally include information related to performing differential centrifugation, flow cytometry (e.g., fluorescence-activated cell sorting) and/or calculating results. Such general information is as previously described.

V. Modulating Immune Response and Treating a Disordered Immune Response in a Patient.

Tumor necrosis factor-α (TNF-α) predominates in the initial phases of sepsis and is one of the first cytokines released into the circulation during the inflammatory response to infectious stimuli. It has diverse effects in vivo as a mediator of the immune response, in part, through activation of neutrophils.

Several papers have described generation of NDMPs following TNF-α administration; however, these papers use TNF-α in conjunction with other agents and do not address the mechanisms or the role of TNF-α in NDMP generation. The present investigators have surprisingly demonstrated that NDMPs are generated by administration of TNF-α alone, and have elucidated the role of TNF Receptor 1 (TNFr1) and TNF Receptor 2 (TNFr2), as well as MP generation as it relates to pathways involved in apoptosis and cellular fate decisions, namely the caspase and NF-κB pathways, thereby permitting development of methods for modulating immune response and for treating diseases relating to a disordered immune response, such as sepsis, pneumonia and systemic inflammatory response syndrome. (Caldwell, Charles C. et al. "Mechanisms underlying mouse TNF-α stimulated neutrophil derived microparticle generation" *Biochem and Biophys Res. Comm.* 437 (2013) pp 591-596, the full disclosure of which is incorporated herein by this reference)

As detailed empirically in Example 19 and illustrated in FIG. 22, treatment of neutrophils with TNF-α increases levels within 30 min. Further, activation of either TNFr1 or TNFr2 is sufficient for NDMp generation, and activation of both is additive (FIG. 23). Upon the selective activation of TNFr1, NDMP numbers were sharply decreased but not entirely eliminated with addition of Caspase 8 inhibitor. In contrast, Caspase 8 inhibition did not alter NDMP numbers when only TNFr2 was activated (FIG. 24). Upon activation of either TNFr1 or TNFr2, the inhibition of NF-κB activity significantly ameliorates NDMP generation (FIG. 25).

According to one embodiment, a method of treating a disordered immune response in a patient is provided. The disordered immune response may be associated with sepsis, pneumonia or systemic inflammatory response syndrome. The method comprises modulating a concentration of neutrophil-derived microparticles (NDMP) in a sample from the patient. Modulating, in accordance with the instant disclosure, means to adjust or regulate, indirectly or directly, for the purpose of achieving a therapeutic goal. Generally, therapeutic goals may include amelioration of severity of symptoms, restoration of normal immune system homeostasis, decrease in NDMP concentrations, elimination of infection, and the like. Samples comprise physiologically relevant samples, for example brachial lavage fluid in the case of a patient suffering from pneumonia and abdominal fluid in the case of a patient suffering from sepsis.

In specific embodiments, modulating is effectuated by modulating tumor necrosis factor-α (TNF-α) activated induction of NDMP generation in the patient. Where the desired modulation is increasing NDMP generation/levels, one or both of TNF-α and a TNF-α receptor agonist may be administered. Where the desired modulation is decreasing NDMP generation/levels, a TNF-α inhibitor may be administered. A TNF-α inhibitor may, for example, comprise a TNF receptor 1 (TNFr1) antagonist, a TNF receptor 2 (TNFr2) antagonist, a TNFr1 and TNFr2 antagonist, or combinations thereof. Caspase 8 is an enzyme known to be involved in cell apoptosis and activation. The present investigators determined that TNFr1 activation generates microparticles partially through a caspase-8 dependent pathway and that microparticle generation through activation of TNFr2 is independent of the caspase-8 pathway. Hence, inhibition of caspase-8 effectuates decreasing NDMP generation/levels and very specific embodiments are directed to administering a caspase-8 inhibitor. According to even more specific embodiments, the caspase-8 inhibitor comprises Z-IETD-FMK.

The present investigators further demonstrated that NDMP generation through TNFr1 and TNFr2 is NF-κB dependent. The NF-κB pathway is activated after cellular TNF-α stimulation. Hence, inhibition of NF-κB will decrease NDMP generation/levels and another specific embodiment is directed to decreasing NDMP generation/levels by administering an NF-κB inhibitor. According to a very specific embodiment, the NF-κB inhibitor is BAY 11-7085.

EXAMPLES

The following non-limiting examples illustrate and/or elucidate specific embodiments of the present disclosure.

Example 1

Figure 1:
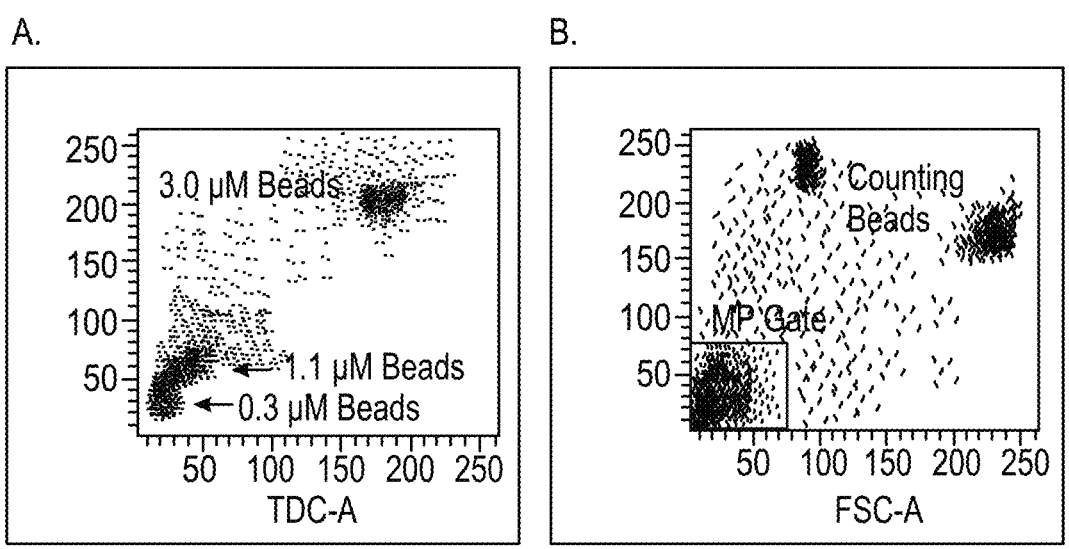
FIG. 1 is a graphical representation of a flow cytometric method for analyzing microparticles wherein: (A) latex beads of a pre-determined size were used to set the forward and side scatter voltages to best distinguish particles ranging from 0.3 to 3.0 µM; and (B) representative gating demonstrated a sizing strategy to detect microparticles.

Detection and Characterization of MPs Isolated from BALf from Critically Ill Patients Experimental Protocol. MPs were isolated from BALf by differential centrifugation consisting of three spins. The first centrifugation (450×g, 10 minutes, 4° C.) was conducted to pellet the cells. The cell pellet from this step may then be used to determine cell activation or apoptosis. The second centrifugation (9,900×g, 5 minutes, 4° C.) was conducted to pellet platelets. The platelet poor supernatant was then subjected to a third spin (17,000×g, 20 minutes, 4° C.). The third spin was conducted to pellet the MPs and to leave soluble proteins and membrane fragments in the supernatant. The resulting MPs were then analyzed by flow cytometry using LSR II Flow Cytometer and FACS Diva Software (BD Biosciences, San Jose, Calif.). As shown in FIG. 1(A), to ensure proper gating upon the correct size of MPs, latex beads of a pre-determined size were used to set forward and side scatter voltages to set the MP gate. Such latex beads were used to best distinguish particles ranging from 0.3 to 3.0 μM. Additionally, as shown in FIG. 1(B), while analyzing MPs by flow cytometry, the addition of a known concentration of two populations of counting beads were included to allow enumeration of NDMP numbers.

Figure 2:
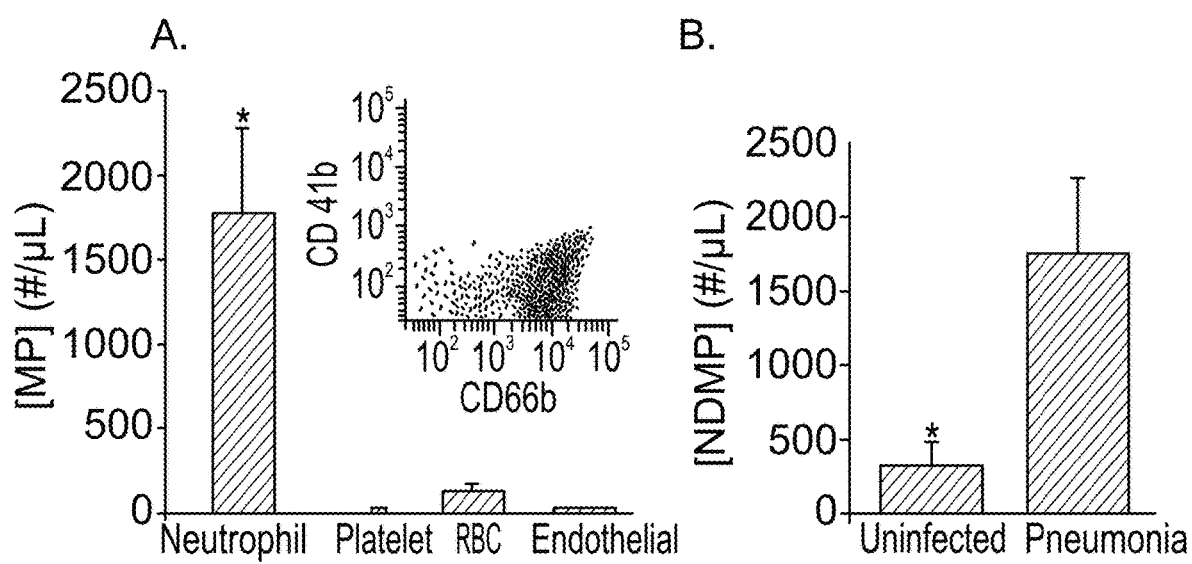
FIG. 2 is a bar graph of (A) microparticles isolated from critically ill patient BALf were predominantly derived from neutrophils, and (inset) is a representative dot plot demonstrating the robust presence of NDMPs; and (B) flow cytometric analysis demonstrating increased NDMP numbers in bacterial infected lungs, wherein the sample size=20 for infected lungs and n=5 for uninfected lungs, *, p<0.05 as determined by ANOVA pairwise comparison for A, and by Student T test for B.

Experimental Results. As shown in FIG. 2(A), it was observed that NDMPs were predominant in the BALf. Moreover, as shown in FIG. 2(B), significantly higher amounts of NDMPs were discovered in infected lungs as compared to non-infected lungs. In other experiments (data not shown), MPs derived from T cells or macrophages were not observed. Accordingly, NDMPs are the predominant MP generated in the lung during pneumonia.

Example 2

Ingestion of NDMPs by Monocytes

Experimental Protocol. Studies have shown that MPs express the apoptosis marker, phosphatidyl serine (hereinafter "PS") on the extracellular leaflet of the plasma membrane. Accordingly, the active phagocytosis of NDMPs was investigated. Specifically, NDMPs were isolated from BALf of pneumonic patients. The NDMPs were then labeled with 5-(and 6)-carboxyfluorescein diacetate (hereafter "CFSE", Invitrogen, Carlsbad, Calif.). An equal volume of 10 mM CFSE was diluted to 1:5000 in PBS just before use. MPs and CFSE were mixed in a 1:1 volume ratio and incubated for 8 minutes at room temperature on a rocker. An equal volume of fetal bovine serum (hereinafter "FBS", Invitrogen) was added and allowed to sit for 1 minute at room temperature. Next, an equal amount of sterile K5 media was added to the mixture and centrifuged at 16,000 g for 30 minutes to pellet MPs. CFSE-labeled NDMPs were incubated with THP-1 cells (ATCC, Manassas, Va.), a human monocytic cell line, at 37° C. in a $CO_2$ incubator overnight. THP-1 cells were collected and analyzed for macrophage activation as determined by HLA-Dr, CD80, and CD86 mean fluorescence intensity (hereinafter "MFI"). THP-1 cells were gated upon CD14 and CD1 1b surface expression and CFSE fluorescence was determined by flow cytometry.

Figure 3:
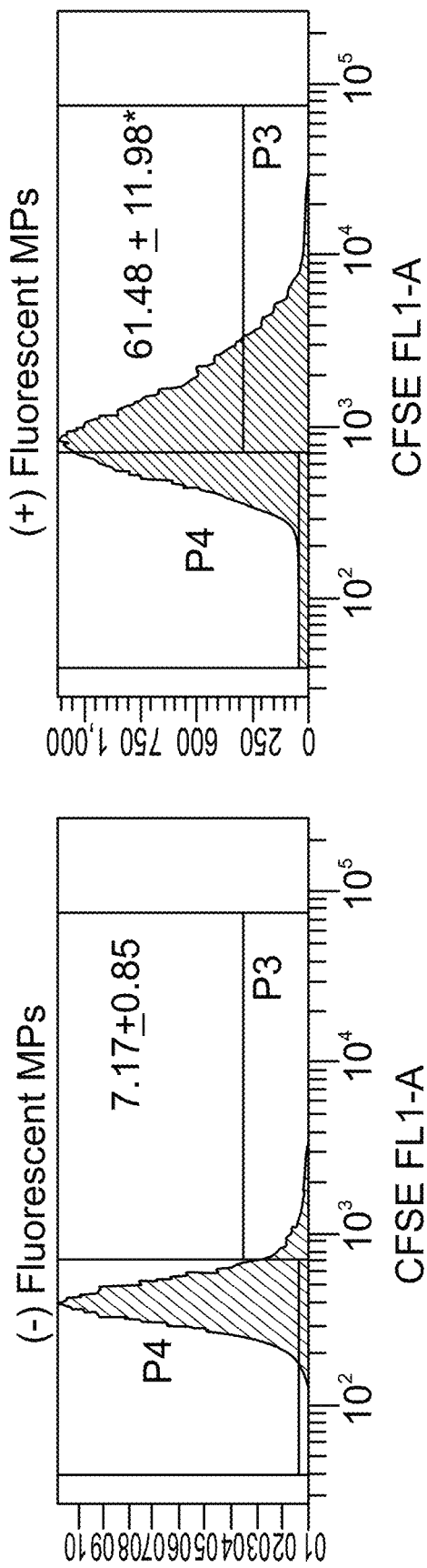
FIG. 3 is a graphical representation of BALf microparticles isolated from pneumonic patients incubated with THP-1 cells for 24 H gated upon CD14, CD11b surface expression determined by flow cytometry of (A) unlabeled BALf microparticles; and (B) BALf microparticles labeled with CFSE, wherein five independent samples were assayed, * p<0.05 as determined by Student T test.

Experimental Results. As shown in FIGS. 3(A)-(B), an increase in fluorescence was observed in the FL-1 (i.e., CFSE-specific) channel from 7.17% to 61.48%. Such data indicates either increased adherence or ingestion of NDMPs.

Example 3

Activation of Monocytes Treated with NDMPs

Experimental Protocol. To determine the impact of ingestion of NDMPs by THP-1 cells, NDMPs were labeled with CFSE as previously described and incubated with THP-1 cells. The use of CFSE-labeled NDMPs allowed discrimination between THP-1 cells that had ingested NDMPs versus THP-1 cells that did not ingest NDMPs (i.e., "bystander cells"). After 18 H, cells were collected and mixed with opsonized Fluoresbrite Polychromatic Red Plain Microspheres 1.0 µM (Polysciences, Warrington, Pa.). The suspension was incubated at 37° C. for 30 minutes. After the incubation period, the phagocytosis was stopped by washing twice. Samples were run on a Becton Dickinson LSR II (BD Biosciences) to determine MFI of (+)CFSE THP-1 and (−)CFSE THP-1 cells as a measure of phagocytosis. To determine macrophage activation status, the cell surface markers HLA-Dr, CD80, and CD86 were fluorescently quantified for THP-1 cells that ingested MPs, bystander cells, and untreated THP-1 cells.

Figure 4:
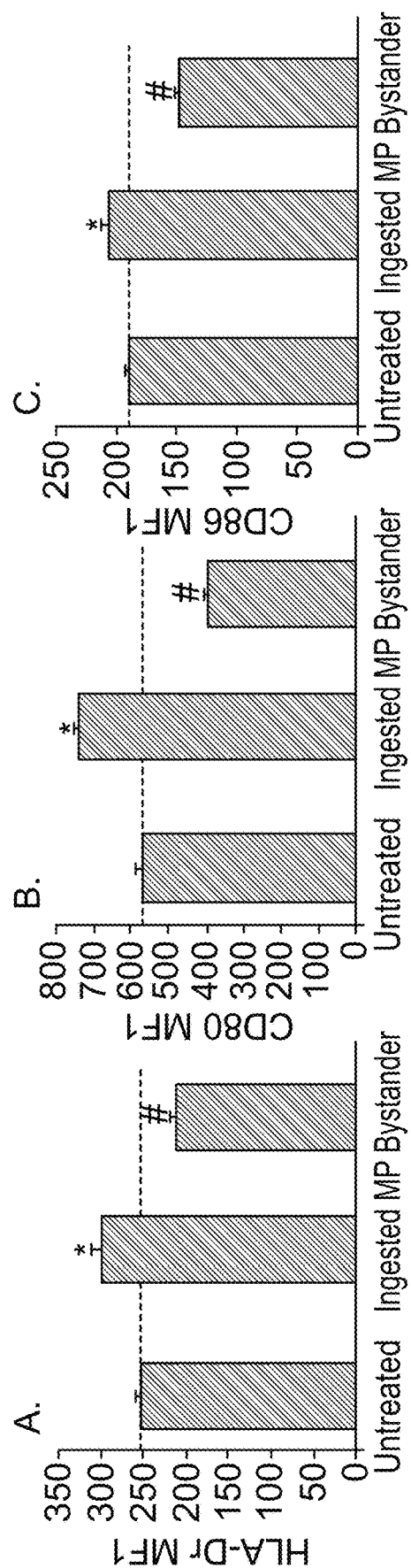
FIG. 4 is a bar graph of fluorescently labeled NDMPs from critically ill patients incubated 18 H with THP-1 cells and compared with untreated and bystander cells analyzed for (A) HLA-Dr; (B) CD80; or (C) CD86 surface expression, wherein six independent BALf samples were assayed, *, p<0.05 as compared to untreated and bystander and #, p<0.05 as compared to ingested as determined by ANOVA pair-wise comparison.

Experimental Results. As shown in FIG. 4, THP-1 cells that ingested NDMPs had increased activation as compared to both untreated and CFSE(−) THP-1 cells. Cells that had ingested NDMPs had increased activation as seen by an increase in the MFI of HLA-Dr, CD80, and CD86 as compared with both untreated and bystander cells. Further, bystander cells exhibited decreased activation as indicated by a decrease in these surface markers. Accordingly, without being bound by the theory, it is believed that NDMPs have a divergent impact upon macrophage phenotype.

Example 4

Functional Effect of Ingestion of NDMPs on THP-1 Cells

Experimental Protocol. THP-1 cells were incubated with CFSE-labeled NDMPs. After 18 H, the cultured cells were incubated with red fluorescent microspheres as previously described. Phagocytic ability was evaluated with flow cytometry.

Figure 5:
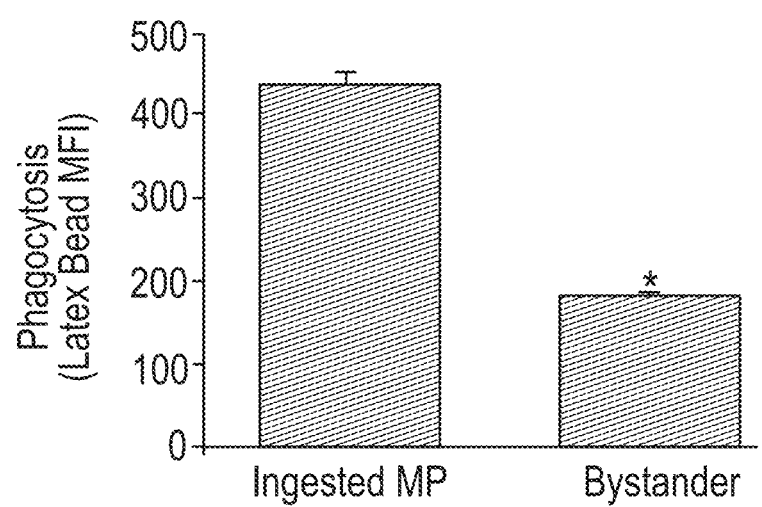
FIG. 5 is a bar graph of (+)CFSE THP-1 cells (Ingested MP) and (−)CFSE THP-1 cells (Bystander) incubated with CFSE-labeled NDMPs for 18 H with respect to phagocytosis, wherein data are expressed as the mean (SEM) and * p<0.05 as determined by Student's t test.

Experimental Results. As shown in FIG. 5, cells that had ingested NDMPs showed an increased phagocytic ability when compared with bystander cells.

Example 5

Development of Model for In Vitro Generation of NDMPs

Experimental Protocol. Peritoneal lavage cells from mice made septic by cecal ligation and puncture were isolated. The cells were then incubated with or without lipopolysaccharide (hereinafter "LPS", 100 ng/mL) for 18 H. MPs from these cultures were then isolated, quantified by bicinchoninic acid assay (hereinafter, "BCA"), and analyzed by fluorescence-activated cell sorting (hereinafter "FACS").

Figure 6:
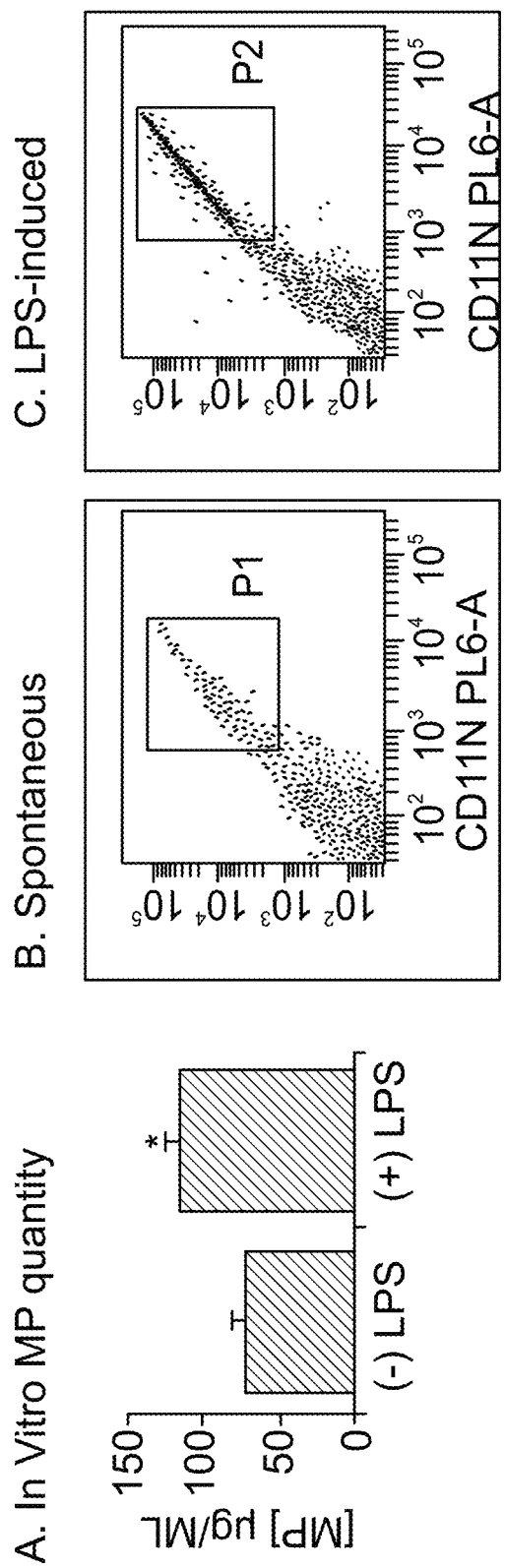
FIG. 6 is a graphical representation of MPs isolated from peritoneal cells of septic mice either left untreated or treated with LPS (100 ng/mL) for 18 H of (A) a bar graph of MPs quantified by BCA, n=4; (B) flow cytometric analysis demonstrating spontaneous generation of MPs; and (C) flow cytometric analysis demonstrating LPS-induced generation of MPs.

Experimental Results. Referencing FIGS. 6(A)-(C), a predominant increase in MPs was due to an approximate 60% increase in NDMPs from LPS-treated cells compared to spontaneous NDMP generation.

Example 6

Variation of In Vivo Lung NDMP

Experimental Protocol. Representative BALf were collected and MPs characterized as previously described. Pathogens were identified by BALf 72 H after collection.

Figure 7:
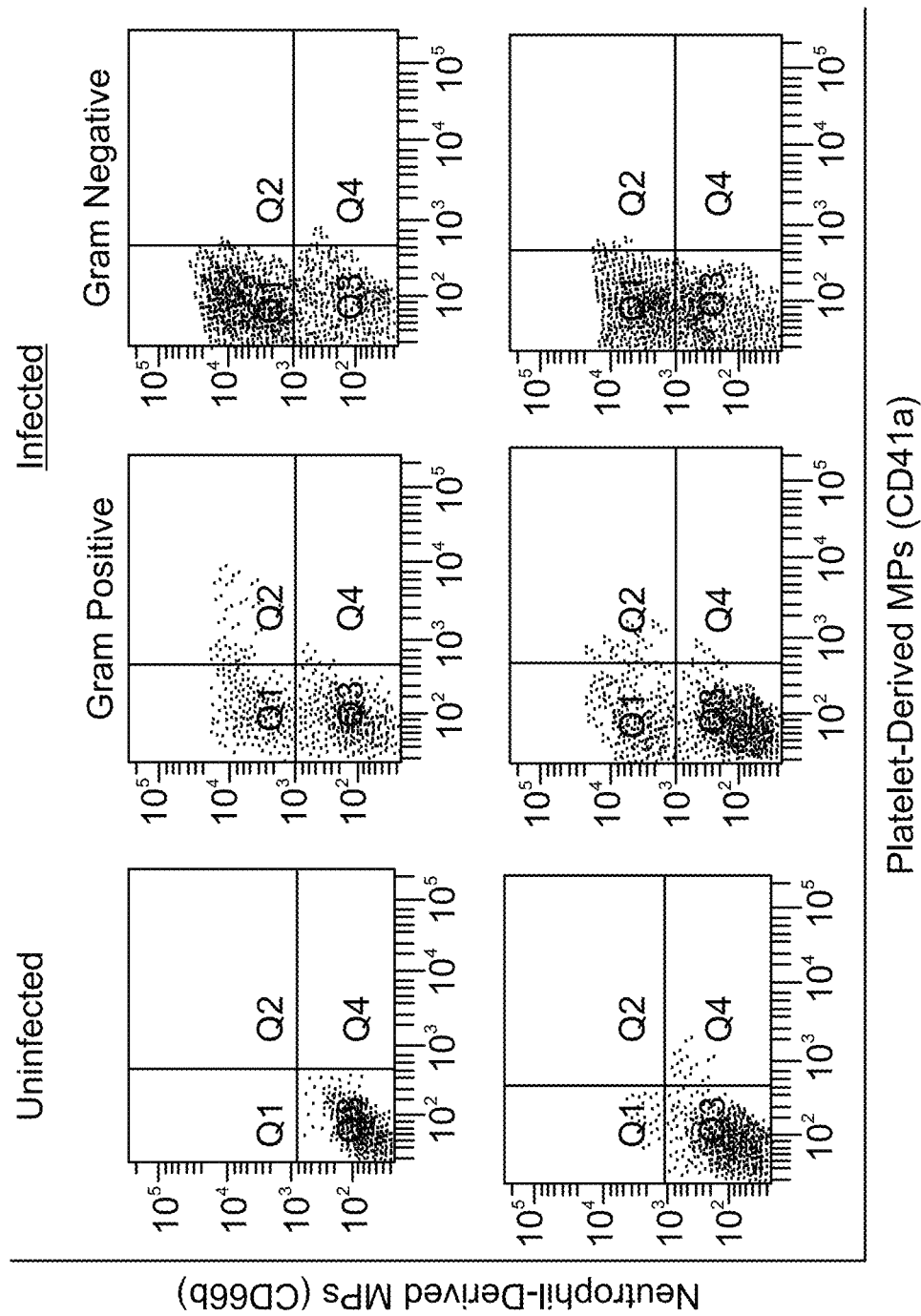
FIG. 7 is a graphical representation of a flow cytometric method for analyzing microparticle isolated from BALf collected from uninfected and infected patients (gram positive and gram negative) wherein pathogens were identified by BALf 72 H after collection.

Experimental Results. As shown in FIG. 7, gram-negative bacteria generate a greater proportion of NDMPs than gram positive bacteria.

Example 7

Neutrophils are Observed at Infectious Foci in Humans and are Neutrophil Derived Experimental Protocol. Abdominal fluid or BALf (between 2 mL and 20 mL) was obtained from patients from the 34-bed surgical ICU of University Hospital (Cincinnati, Ohio). More specifically, abdominal fluid was obtained from 4 patients undergoing exploratory laparotomy for peritonitis and 4 patients undergoing elective abdominal surgery. All patients with a visceral perforation accompanied with a gross contamination of the abdomen were considered septic (n=3). Patients undergoing elective abdominal surgery was used as a nonseptic control (n=4). Patients were diagnosed with sepsis by the treating surgical intensivist following the American College of Chest Physicians/Society of Critical Care Medicine definition, defined as those patients meeting two of the four systemic inflammatory response syndrome criteria with an infectious process. BALf was obtained from 33 surgical patients with critical illness or injury undergoing diagnostic fiberoptic bronchoscopy with bronchoalveolar lavage (hereinafter "BAL") based on an institutional protocol for the diagnosis of ventilator-associated pneumonia (hereinafter "VAP"). Indications for BAL for suspected VAP were defined by ICU guidelines as the appearance of a new or changing infiltrate on chest radiograph or macroscopically purulent sputum plus at least two of the following: temperature higher than 38° C. or lower than 36° C., white blood cell count higher than $12,000/mm^3$ or lower than $4000/mm^3$, 10% bands, heart rate higher than 90 beats per minutes, respiratory rate higher than 20 breaths per minute, or $PaCO_2$ lower than 32 mm Hg. Two BAL samples from lung donors were obtained and used as an uninfected control in the subset of patients with suspected pneumonia.

Peritoneal waste fluid was collected in sterile 50-mL conical tubes from patients that underwent exploratory laparotomy or elective abdominal surgery in which abdominal irrigation was performed. Fluid was immediately placed on ice for MP analysis within 2 hours of collection time. All patients with a clinical suspicion of VAP underwent diagnostic fiberoptic bronchoscopy with BAL. All BAL procedures were performed in a uniform manner by the treating surgical intensivist as part of ICU clinical practice guidelines. The bronchoscope was advanced into the lung segment wherein radiographic changes were seen. After the bronchoscope was wedged into the appropriate lung segment, 20 mL of sterile saline was instilled into the lung as a wash. The waste BAL effluent was collected in a sterile specimen trap and immediately placed on ice for MP analysis within 2 hours of collection time. Abdominal fluid and BAL fluid (i.e., BALf) samples were collected as unidentifiable surgical waste that could not be linked back to the investigator.

Upon obtaining the abdominal fluid or BALf (between 2 mL and 20 mL), the fluid was kept on ice until the time of processing. Fluid samples were initially filtered using a 150-µm, sterilized stainless steel mesh into a sterile 50-mL conical tube. Cells in the fluid were pelleted after a 10-minute 450 g centrifugation. The supernatant was then centrifuged for 10 minutes at 9,900 g to remove platelets. The platelet-free supernatant was centrifuged for 20 minutes at 16,000 g to pellet MPs. The MP pellet was resuspended in 500 µL of sterile phosphate-buffered saline (i.e., PBS) and centrifuged for 20 minutes at 16,000 g. The MP pellet was then resuspended in 100 µL of sterile PBS for analysis.

The analysis of cell surface antigen expression was performed on abdominal fluid and BALf. Flow cytometry data acquisition and analysis were performed on an LSR II using FACS Diva software (BD Biosciences, Mountain View, Calif.). The antibodies used were as follows: CD66b (clone G10F5; BD Biosciences), CD105 (clone 43A3; BioLegend), CD41a (clone HIP8; BD Biosciences), CD235 (clone HIR2; BioLegend), CD14 (clone M5E2; BioLegend), CD11b (clone M1/70; BioLegend), HLA-Dr (clone L243; BD Biosciences), HLA-Dr (clone L243; BD Biosciences), CD80 (clone L307.4; BD Biosciences), and CD86 (clone 2331; BD Biosciences).

Statistical comparisons were performed using Student's t test (two groups) or one-way ANOVA with Holm-Sidak post hoc test (more than two groups) using StatView 3.5 (SAS Institute, Cary, N.C.). The mean and standard error of the mean were calculated in experiments containing multiple data points; $p<0.05$ was considered statistically significant.

Figure 8:
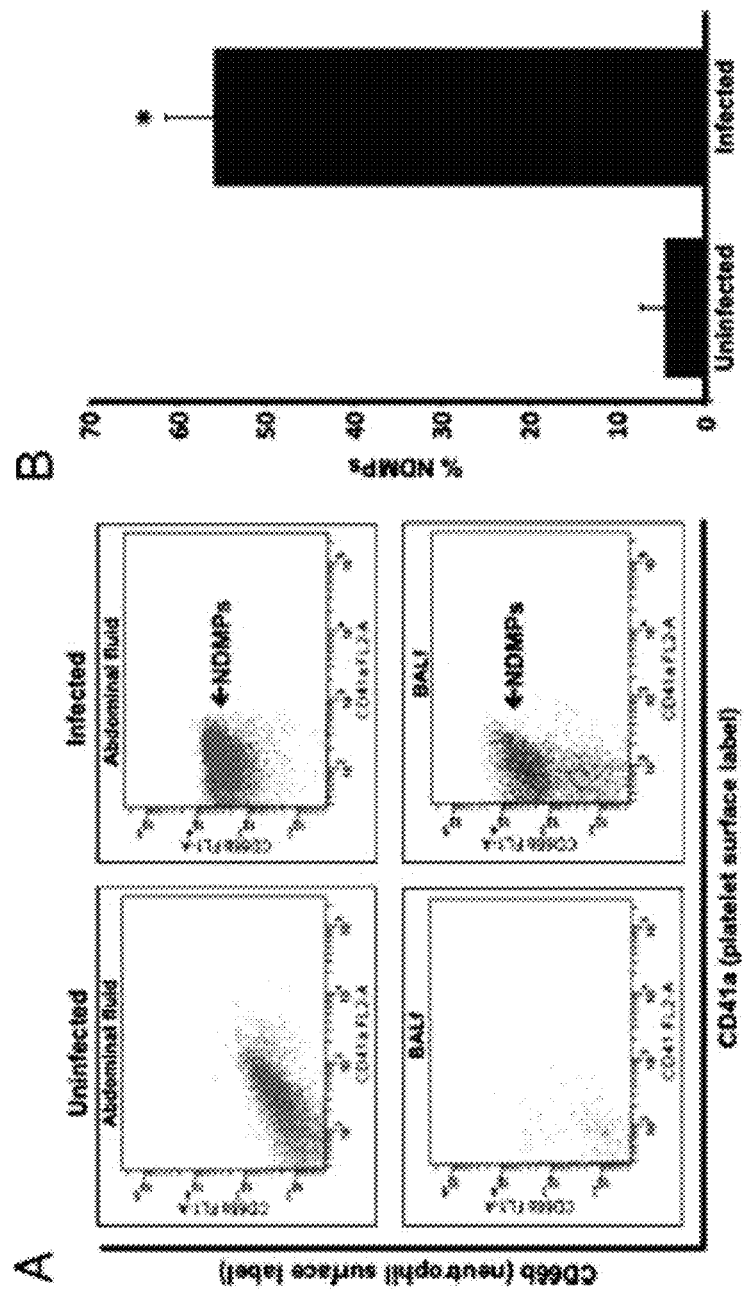
FIG. 8 is a graphical representation of (A) NDMPs isolated from abdominal irrigation fluid obtained from patients undergoing exploratory laparotomy for peritonitis (infected) or elective surgery (uninfected) and from BALf obtained from patients with suspected pneumonia (infected) or lung donors without pneumonia (uninfected); and (B) flow cytometric analysis demonstrating increased NDMP numbers in abdominal infections, wherein n=3 for infected abdomens, and n=4 for uninfected abdomens.

Experimental Results. As shown in FIGS. 8(A)-(B), an increased number of MPs were present in the abdomen of patients with peritonitis when compared with healthy controls. Additionally, as shown in FIG. 8(A), the MPs in the abdomen of patients with peritonitis were primarily derived from neutrophils. Additionally, as shown in FIG. 8(B), MPs were present in the BALf from patients with suspected pneumonia. Such MPs were primarily derived from NDMPs.

Example 8

MPs are Observed at Infectious Foci in Humans and Mice During Sepsis

Experimental Protocol. MPs were isolated from peritoneal washes by differential centrifugation consisting of three steps. The first centrifugation (450×g, 10 minutes, 4° C.) was conducted to pellet the cells. The second spin pelleted platelets (9,900×g, 5 minutes, 4° C.). The platelet-poor supernatant was then subjected to a third spin (17,000×g, 20 minutes, 4° C.). This pelleted the MPs and left soluble proteins and membrane fragments in the supernatant. These resulting MPs were then analyzed by flow cytometry. To ensure proper gating for the correct size of MPs, latex beads of known sizes were used to set the MP gate. For mice, a moderately severe CLP was induced and peritoneal lavages were conducted. For humans, de-identified excess abdominal irrigation fluid was provided from non-infected or septic patients. Both mouse and human samples underwent differential centrifugation as described to selectively isolate MPs. MPs were then labeled with antibodies against CD3 (T cell), CD66b or Ly-6G (human or mouse neutrophil markers, respectively), CD105 (endothelial cell marker), CD41 (platelet marker), and CD14 or F4/80 (human or mouse macrophage markers, respectively).

Figure 9:
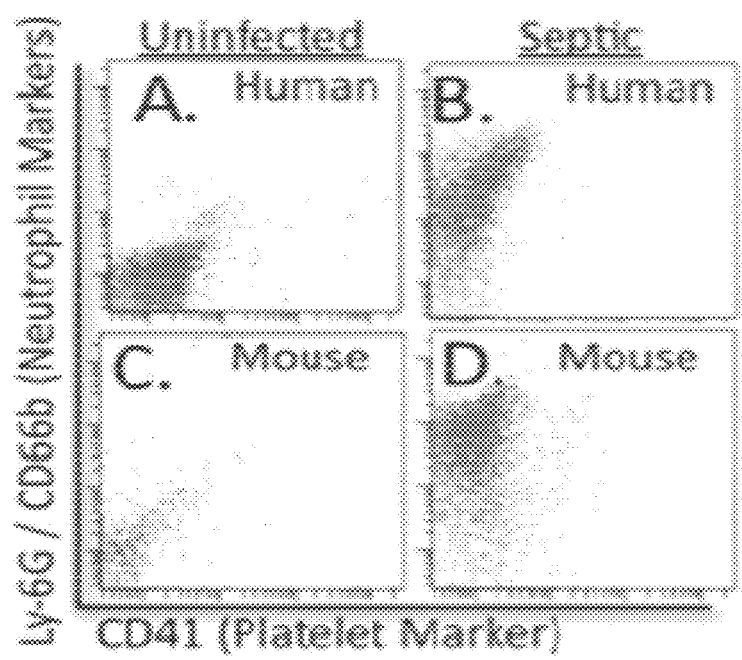
FIG. 9 is a graphical representation of a flow cytometric method for analyzing NDMPs and platelet microparticles isolated from (A) peritoneal surgical waste fluid from uninfected patients; (B) peritoneal surgical waste fluid from peritonitis patients; (C) sham-operated mice; and (D) CLP-operated mice, wherein samples were analyzed using an LSR II flow cytometer and FACS Diva software.

Experimental Results. As shown in FIGS. 9(A) and 9(C), in humans and mice, significant amounts of MPs in samples were not identified from uninfected hosts. However, as shown in FIGS. 9(B) and 9(D), a robust increase in NDMPs was observed in infected hosts. MPs derived from other cell types were not observed (data not shown). Thus, NDMPs are the predominant MPs generated at the infectious focus during sepsis.

Example 9

CLP-Derived NDMPs are Positively Correlated with Sepsis Severity and Can Increase Sepsis Mortality Experimental Protocol. The pathogenecity of NDMPs during sepsis was investigated. First, serum IL-6 levels were quantified from septic and non-septic mice at 6 H and the correlation of this with peritoneum NDMP numbers was calculated. A positive correlation (n=14, r=0.8, p=0.0007) was observed, indicating that NDMPs are associated with increased sepsis severity. Next, sepsis was inflicted on mice with exogenously added NDMPs. NDMPs were also tested for endotoxin. More specifically, CLP-derived NDMPs were tested for endotoxin using a Limulus Amoebocyte Lysate Assay. It was observed that the CLP-derived NDMPs contained significant amounts of endotoxin (~875 EU/mL) (data not shown).

To determine whether the endotoxin was free-floating (i.e., in the wash) or bound to the MPs, we subjected CLP-derived MPs to multiple washes. After each wash, the number of MPs present as well as the endotoxin concentration associated with the MP pellet were calculated. The ratio of endotoxin associated with each MP was also calculated. Without being bound by the theory, it was postulated that if the endotoxin/MP ratio decreased after each wash, the endotoxin was free-floating.

Low-endotoxin NDMPs were generated and used to assess host response during sepsis. More specifically, mice were treated with intraperitoneal injections of 3% thioglycolate (hereinafter, "TGA"), LPS, or petidylglycan (hereinafter "PepG"). Peritoneal neutrophil recruitment, NDMPs, and endotoxin associated with NDMPs were quantified.

Figure 10:
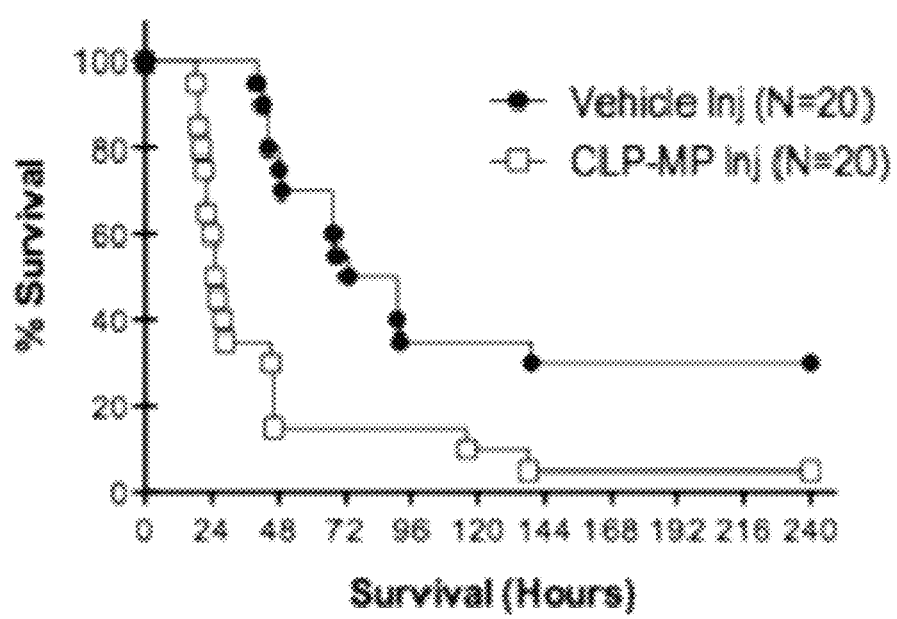
FIG. 10 is a graph of survival (H) of mice undergoing CLP intraperitoneally injected with saline vehicle or a bolus of MPs in saline (65,000) isolated from previously CLP-operated mice with respect to survival (%), wherein survival was monitored for 10 days and data were combined from 3 independent experiments, each demonstrating the same trend, p=0.0004 as determined by log-rank (Mantel-Cox) test.

Experimental Results. As shown in FIG. 10, mice injected with a bolus of NDMPs suffered increased mortality as compared to vehicle-injected mice. As shown in FIG. 11, the endotoxin/MP ratio remained constant after repeated washes. Accordingly, it is believed that CLP-derived MPs have bound endotoxin which cannot be removed by conventional means. As shown in Table 1 below, treatment with TGA, LPS, and PepG resulted in neutrophil recruitment and NDMP generation. Moreover, treatment with 3% TGA resulted in the greatest number of low endotoxin NDMPs.

TABLE 1

| Treatment with TGA, LPS, or PepG | | | |
|---|---|---|---|
| Treatment: | # Neuts (×10$^6$) | # NDMPs (×10$^3$) | [Endotoxin] (EU/mL) |
| None | 0.0024 | 0.114 | 23.2 ± 15 |
| CLP | 7.3 | 64.5 | 875 ± 494 |
| 3% TGA | 6.9 | 35.1 | 26.4 ± 16.5 |
| PepG | 2.0 | 3.0 | 37.4 ± 31 |
| LPS | 0.16 | 2.4 | 131.9 ± 25.7 |

Treatments:
CLP - 75% ligation/(1) 23 gauge puncture (~50% survival),
3% TGA - 1 mL 3% Thioglycolate i.p. injection,
PepG - 1 mg peptidoglycan, i.p. injection,
LPS - 100 μg LPS i.p. injection Example 10

Exogenous Low Endotoxin TGA-Derived NDMPs Increase Sepsis Mortality

Experimental Protocol. Peritoneal MPs were isolated from TGA-treated mice. Endotoxin-free saline vehicle or MPs (65,000) in saline were intraperitoneally injected as a bolus into cohorts of mice undergoing CLP. Survival was monitored for 10 days.

Experimental Results. As shown in FIG. 12, mice injected with a bolus of 65,000 NDMPs exhibited increased mortality as compared to vehicle-injected mice. Importantly, median survival times were significantly different between mice injected with CLP-derived MPs (25.5 H) and those injected with TGA-derived MPs (42 H). Accordingly, it is believed that endotoxin-free NDMPs have a negative impact upon survival during sepsis beyond adding to endotoxin levels.

Example 11

NDMPs Can Be Ingested by Macrophages

Experimental Protocol. MPs were isolated from septic mice and analyzed for PS expression. Additionally, CFSE-labeled MPs were incubated with macrophages for 3H and phagocytosis was determined by AMNIS and by flow cytometry. More particularly, multispectral imaging flow cytometric analysis (i.e., Amnis ImageStream X) was used to determine the localization of fluorescently (i.e., CFSE) labeled NDMPs within phagocytes after 3 H incubation. Finally, with regard to flow cytometry, CD68 and CD11b positive macrophages were gated upon and fluorescence was observed.

Experimental Results. As shown in FIG. 13(A), it was observed that approximately 80% of NDMPs express extracellular PS. Additionally, as shown in FIG. 13(B), localization of fluorescently labeled NDMPs within phagocytes was observed. Referencing FIG. 13(C), increased fluorescence was observed in CD68 and CD11b positive macrophages, indicating either adherence or ingestion of fluorescently-tagged NDMPs. Such data indicate that NDMPs can be phagocytosed by macrophages.

Example 12

NDMPs Decrease Host Ability to Clear Bacteria During Sepsis

Experimental Protocol. NDMPs were isolated from TGA-treated mice. A bolus of 65,000 low endotoxin NDMPs or vehicle was intraperitoneally injected into mice undergoing CLP. After 24 H, the mice were sacrificed and peritoneal cells were evaluated for phagocytic ability by flow cytometry (n=10/group). Viable bacteria in blood were also quantified by flow cytometry (n=6).

Experimental Results. As shown in FIG. 14(A), a 20% decrease in phagocytic ability in mice was quantified in mice that possessed increased numbers of NDMPs. Additionally, as shown in FIG. 14(B), a 2-fold increase in blood bacterial load was observed in mice that possessed increased NDMPs. Accordingly, it is believed that NDMPs compromise the host ability to localize an infection.

Example 13

NDMP Incubation Results in Decreased T-Cell CD44 Expression and Numbers

Experimental Protocol. There is an emerging view that T-cell responses are critical within the first hours of sepsis. As such, the impact of NDMPs on T-cells was investigated. First, a bolus of 65,000 TGA-derived NDMPs or vehicle was intraperitoneally injected into non-septic mice for 24 H. After, peritoneal non-naïve T-cells (CD62L$^{low}$) were quantified or analyzed for CD44 expression. CD44 is a transmembrane glycoprotein which binds the major in vivo ligand of T-cells, hyaluronic acid. It has been found to be important in T-cell signaling and function.

Experimental Results. As shown in FIG. 15(A), a significant decrease in the number of peritoneal T-cells in mice injected with TGA-derived NDMPs was observed. Additionally, as shown in FIG. 15(B), a significant decrease in the expression of CD44 was observed in mice injected with TGA-derived NDMPs. Such data indicate that increased NDMPs can contribute to T-cell immune suppression.

Example 14

NDMP Incubation with Macrophages Deactivates Macrophages

Experimental Protocol. To determine the impact of ingestion of NDMPs by macrophages, a bolus of 65,000 low-endotoxin TGA-derived NDMPs or vehicle was intraperitoneally injected into non-septic, naïve mice. After 24 H, peritoneal macrophages were evaluated for Cd1 lb and MHCII surface expression by flow cytometry. Ex vivo peritoneal macrophages were also assessed for intracellular TNF-α production after in vitro activation by 100 ng/mL LPS.

Experimental Results. As shown in FIGS. 16(A)-(B), decreased expression of CD11b and MHCII were observed in mice injected with TGA-derived NDMPs. Additionally, as shown in FIG. 16(C), decreased TNF-α production was significantly decreased. Altogether, the data indicates that NDMP incubation with macrophages depresses antigen presentation ability and functionality.

Example 15

LPS Augments Spontaneous NDMP Formation In Vitro

Experimental Protocol. Peritoneal cells were isolated from septic mice 24 H after CLP. The isolated peritoneal cells were incubated with PBS or 100 ng/mL LPS for 24 H. Samples were analyzed using LSR II flow cytometer and FACS Diva software (BD Biosciences). As shown in FIG. 17(A), latex beads of a predetermined size were used to set the forward and side scatter voltages to best distinguish particles ranging from 0.3 to 1.0 µM.

Experimental Results. Referencing FIGS. 17(B)-(C), LPS treatment was observed to enhance NDMP formation from peritoneal cells isolated from septic mice.

Example 16

Spontaneous NDMP Generation is Increased with Elevated cAMP

Experimental Protocol. Signaling intermediates required for NDMP formation are largely unexplored. cAMP was targeted as a potential signaling mechanism involved in NDMP formation. Peritoneal cells were isolated 24 H after CLP surgeries. The isolated peritoneal cells were incubated with either saline vehicle, 10 µM 8-Br cAMP (i.e., a membrane-permeable non-hydrolyzable cAMP analog), or 20 µM H89 (i.e., a PKA inhibitor). After 24 H, NDMPs were enumerated and characterized by flow cytometry.

Experimental Results. As shown in FIG. 18, significant spontaneous NDMP generation was observed. Additionally, it was further observed that increased intracellular cAMP augmented the spontaneous generation of NDMPs. Accordingly, such data indicate that NDMP formation does not require active PKA, but that PKA activity is sufficient to increase NDMP formation.

Example 16

TGA Generates Microparticles In Vivo

Experimental Protocol. The ability of TGA to generate microparticles in vivo was investigated. Male C57BL/6 mice between 6 and 8 weeks of age (about 20 to 28 g) were injected in the peritoneum with 1 mL 3% thioglycolate (Sigma, St. Louis, Mo.) or with vehicle. Peritoneal lavage was performed 24 H after injection. Peritoneal cells were pelleted after a 10-minute 450 xg centrifugation. The supernatant was then centrifuged for 10 minutes at 9,900×g to remove platelets. The platelet-free supernatant was centrifuged for 20 minutes at 16,000×g in order to pellet MPs. The MP pellet was resuspended in 500 µL sterile PBS and centrifuged for 20 minutes at 16,000×g. The MP pellet was then resuspended in 100 µL sterile PBS for analysis.

Analysis of cell surface antigen expression was performed on peritoneal lavage fluid. Flow cytometry data acquisition and analysis were performed on an LSR II using FACS Diva software (BD Biosciences). Antibodies used included: Ly-6G (Clone: 1A8, BioLegend), LY-6C (Clone: AL-21, BD Biosciences), CD11b (Clone: M1/70, BioLegend), Ter-119 (Clone: Ter-119, BioLegend), CD41 (Clone: MWReg30, BioLegend), CD105 (Clone: MJ7/18, BioLegend), Annexin V (BioLegend), and counting beads (Invitrogen, Grand Island, N.Y.). As shown in FIG. 19(A), forward and side scatter flow cytometry were initially performed on the lavage to both characterize and enumerate microparticles. A gate was created using 0.3-1.1 µm beads to isolate the MPs in the sample.

Vehicle mice and TGA-treated mice were stained with neutrophil specific Ly6G and annexinV antibodies. Total NDMPs from TGA-treated mice and vehicle mice were then enumerated.

Experimental Results. As shown in FIGS. 19(B)-(C), NDMPs were observed in vehicle mice and TGA-treated mice. Additionally, as shown in FIG. 19(D), a robust accumulation of NDMPs in the TGA-treated mice was observed in comparison with the untreated mice. Such data indicate that TGA can effectively be used to generate microparticles in vivo.

Example 17

NDMP Generation is Dependent on the Caspase Pathway

Experimental Protocol. A biochemical pathway for NDMP formation was investigated. Specifically, proteins associated with F-actin were investigated, as F-actin rearrangement is a terminal step in apoptosis. The role of myosin light chain kinase (hereinafter "MLC K") in NDMP generation was initially investigated. Peritoneal cells were isolated from peritoneal lavage 24 H after 1 mL 3% TGA injection. Peritoneal cells were cultured with one of the following agonists or inhibitors overnight in a $CO_2$ incubator: 250 µM ML7, a MLCK inhibitor, (Tocris, Bristol, UK), 200 µM Z-VAD-FMK, a caspase 3 inhibitor, (Tocris), 30 µM Z-IETD-FMK, a caspase 8 inhibitor, (Tocris), or 30 µM Z-LEHD-FMK, or a caspase 9 inhibitor, (Tocris). Cells and MPs were collected 24 H following incubation and analyzed using flow cytometry as previously described.

Statistical comparisons were performed using Student t Test (two groups), or one-way ANOVA with Holm-Sidak post-hoc test (more than two groups) using StatView 3.5 (SAS Institute, Cary, N.C.). The mean and standard error of the mean were calculated in experiments containing multiple data points. A value of $p \leq 0.05$ was considered statistically significant.

Experimental Results. As shown in FIG. 20(A), peritoneal cells cultured with ML7 demonstrated a 75% decrease in NDMP generation when compared to those cultured without ML7. As shown in FIG. 20(B), inhibition of caspase 3 with Z-VAD-FMK resulted in a 37% decrease in NDMP generation when compared to cells cultured without Z-VAD-FMK. As shown in FIG. 20(C), inhibition of caspase 8 with Z-IETD-FMK resulted in a 37% decrease NDMP generation when compared to cells cultured without Z-IETD-FMK. As shown in FIG. 20(D), inhibition of caspase 9 with Z-LEHD-FMK resulted in no significant difference when compared to cells cultured without Z-LEHD-FMK. These data indicate that NDMP generation is in part dependent on extrinsic apoptosis pathway through caspase 8, caspase 3, through Myosin light chain kinase, and ultimately through F-actin rearrangement.

Example 18

Activation of the cAMP Dependent PKA Pathway can Regulate NDMP Generation

Experimental Protocol. Elucidation of potential signaling pathways involved in NDMP formation was studied. Peritoneal cells were isolated from peritoneal lavage 24 H after 1 mL 3% TGA injection. Peritoneal cells were incubated with one of the following agonists or inhibitors overnight in a $CO_2$ incubator: 100 µM 8-Bromo-cAMP, a cAMP analogue, (Tocris), 20 µM H89 dihydrochloride, a PKA inhibitor (Tocris), 100 µM 6-Bnz-cAMP, a PKA agonist, (Tocris), 100 µM 8-CPT-2Me-cAMP, EPAC, (Tocris), 200 µM Z-VAD-FMK (Tocris), 30 µM Y27632 dihydrochloride, a Rho Kinase Inhibitor, (Tocris), or 250 µM ML 7 hydrochloride (Tocris). Cells and MPs were collected 24 H following incubation and analyzed using flow cytometry as previously described.

Experimental Results. As shown in FIG. 21(A), peritoneal cells cultured with 8-Br exhibited decreased NDMP numbers while peritoneal cells cultured with H89 did not. As shown in FIG. 21(B), peritoneal cells cultured with 6-Bnz-cAMP inhibited NDMP formation compared to cells cultured without 6-Bnz-cAMP. Additionally, as shown in FIG. 21(B), peritoneal cells cultured with EPAC did not affect NDMP numbers compared to cells cultured without EPAC. As shown in FIG. 21(C), peritoneal cells cultured with Y27632 exhibited a decrease in the total number of NDMPs when compared to cells cultured without Y27632. As shown in FIG. 21(D), peritoneal cells cultured with PGE2, known to active cAMP, exhibited a decrease in the total number of NDMPs when compared to cells cultured without PGE2.

The following is generally applicable to Examples 19-22.

Materials and Methods. Male C57BL/6 and TNFr1 KO (stock number: 003242) mice between 6 and 8 weeks of age were obtained from Jackson Labs (Bar Harbor, Me.). Mouse and human TNF-α Recombinant Protein (rmTNF-α and rhTNF-α, respectively) were purchased from Preprotech (Rocky Hill, N.J.). NF-κB inhibitor (BAY 11-7085) and Caspase 8 inhibitor (Z-IETD-FMK) were purchased from R&D systems (Minneapolis, Minn.). The pharmacological agents were solubilized in DMSO (American Bioanalytical, Natick, Mass.). The amount of DMSO was consistent in all samples groups. Neutrophil isolation. Mouse neutrophils from bone marrow were isolated from C57Bl/6 mice as previously described. The femurs and tibias were flushed with Hanks' Balanced Salt Solution without calcium & Magnesium (HBSS) (Mediatech, Inc. Manassas, Va., USA). Bone marrow particulate was disaggregated and filtered in a 70 micron filter, then centrifuged at 400×g for 10 min at 23° C. The cells in the pellet were resuspended in HBSS, placed on a 55% Percoll gradient, and centrigued at 100 xg for 30 min at 23° C. The pellet was washed once more. The final neutrophil preparation was re-suspended in HBSS. The purity and viability of the neutrophils (90% purity>99% viability, respectively) was determined by flow cytometry. Neutrophil purity was assessed by flow cytometry after cell staining with fluorescently conjugated antibodies to Ly-6G, CD19, CD3 and F4/80 with >99% of the cells negative for F4/80 and CD3. The main cell contaminant in this preparation was due to B cells. Further purification was not conducted by centriguation due to risk of non-specific neutrophil activation or by magnetic beads due to microparticle-sized contaminants introduced by the beads themselves.

Microparticle generation and analysis. Isolated neutrophils from bone marrow preparation were plated and cultured for the indicated time at 37° C. with stated treatments. The cell/micropartocle mixture was labeled for Ly-6G and Annexin V without manipulation as previously described. Flow cytometry data acquisition and analysis were performed on a Beckman Coulter Epic flow cytometer using Kaluza software (Indianapolis, Ind., USA). Neutrophil derived microparticle numbers were assessed using the neutrophil specific marker, Ly-6G (Clone: 1A8, BD Pharmingen, San Diego, Calif., United States); and Annexin V (BD Pharmingen). Particles within the 0.3-1.0 μm range that were labeled with both Ly-6G and Annexin V were identified as NDMPs.

Statistical Analysis. Statistical comparisons were performed using Student t Test (two groups), or one-way ANOVA with Tukey post hoc test, (more than two groups) using Prism 5.0 (GraphPad Software, La Jolla, Calif., United States). The mean and standard error of the mean were calculated in experiments containing multiple data points. A value of $p<0.05$ was considered statistically significant.

Example 19

Generation of NDMP by Administration of TNF-α

Using flow cytometry, forward- and side-channels were set to analyze particles using 0.5-, 0.9-, and 3.0-μm latex beads for calibration as previously described (FIG. 22A). The forward and side scatter gate for microparticles was then set based upon size (FIG. 22B). To enumerate NDMPs, neutrophil and NDMP mixture were analyzed with the neutrophil-specific marker, Ly6G, and the apoptosis marker, annexin V. Vesicles within the 0.3-1.0 μm range that expressed both Ly6G and phosphatidylserine were identified as NDMPs. FIG. 22C is representative of NDMP generation after vehicle treatment and FIG. 22D is representative NDMP generation after rmTNF-α treatment. As illustrated in FIG. 22E, 25 ng/mL of rmTNF-α increased the number of NDMPs both at 30 min and at 1 h. Viability of neutrophils was also assessed at these time points and in all subsequent experiments and no significant difference in cell viability was found in regard to treatment (data not shown). Thus, the one-hour time point was used for the experiments described in Examples 19-22.

Example 20

Activation of both TNFr1 and TNFr2 Results in NDMP Generation

To determine the role of these two TNF receptors in NDMP generation, two forms of TNF-α were utilized, (1) rmTNF-α which binds to both TNFr1 and TNFr2 in mice and, (2) recombinant human TNF-α (rhTNF-α) which binds only to TNFr1 in mice. rhTNF-α treatment generated a significantly higher number of NDMPs compared to untreated neutrophils. Further, rmTNF-α generated a significantly higher number of NDMps compared to rhTNF-α (FIG. 23A).

To determine if rhTNF-α was specific for TNFr1 activation, neutrophils from TNFr1−/− mice with either vehicle or rhTNF-α were treated (FIG. 23B). rhTNF-α produced no significant difference in NDMP generation compared to vehicle in TNFr1−/− mice, suggesting that rhTNF-α activates only TNFr1.

TNFr1−/− mice were treated with rmTNF-α. As illustrated graphically in (FIG. 23C), neutrophils from the TNFr1−/− mice treated with rmTNF-α treatment in the WT mice generated significantly more microparticles than the TNFr1−/− mouse. Conclusion: NDMP can be produced after activation of TNFr1 alone or TNFr2 alone, but is robustly increased by the combined activation of TNFr1 and TNFr2.

Example 21

Inhibition of Caspase 8 Diminishes NDMPs Generated through Activation of TNFr1

It is known that TNF-α can activate caspase 8, an enzyme known to be involved in cell apoptosis and activation. Genetically modified mice and specific pharmacological agents with and without caspase 8 inhibitor were utilized (FIG. 24). Activation of TNFr1 alone (rhTNF-α) or TNFr1 and TNFr2 (rmTNF-α) coupled with caspase 8 inhibitor resulted in a significant decrease in NDMPs. Significantly, there was no decrease in microparticle generation from addition of Caspase 8 inhibitor to neutrophils isolated from TNFr1−/− mice. Conclusion: TNFr1 activation generates microparticles partially through a caspase-8 dependent pathway and microparticle generation through activation TNFr2 is independent of the caspase-8 pathway.

Example 22

Inhibition of NF-κB Abrogates NDMPs Generated through Activation of TNFr1 and TNFr2

It is known that the NF-κB pathway is activated after cellular TNF-α stimulation. BAY 11-7085, which inhibits the activation of NFκ-B and the phosphorylation of IκBα, was utilized. As shown in FIG. 25, BAY 11-7085 completely abrogates NDMP generation after activation of TNFr1, TNFr2 or both. Conclusion: NDMP generation through TNFr1 and TNFR2 activation is NF-κB dependent.

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

While particular embodiments of the present disclosure have been illustrated and described, it would be obvious to one skilled in the art that various other changes and modifications can be made without departing from the spirit and scope of the disclosure. It is therefore intended to cover in the appended claims all such changes and modifications that are within the scope of this disclosure.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

What is claimed:

1. An in vitro method for diagnosing and treating sepsis in a human patient, the method comprising:
    (a) contacting at least a portion of a biological sample from the patient consisting essentially of microparticles isolated via differential centrifugation with reagents for detection and/or quantification of neutrophil-derived microparticles, wherein the biological sample is selected from the group consisting of abdominal irrigation fluid and peritoneal waste fluid;
    (b) determining a level of neutrophil-derived microparticles based on the contacting in step (a);
    (c) diagnosing sepsis in the patient when the determined level of neutrophil-derived microparticles is elevated relative to a cutoff value of the neutrophil-derived microparticles; and
    (d) treating the diagnosed patient for sepsis.

2. The method of claim 1, wherein:
    the reagents for detection and/or quantification of neutrophil-derived microparticles comprise at least one antibody having specific binding affinity to the neutrophil-derived microparticles.

3. The method of claim 2, wherein the at least one antibody is fluorescently labeled.

4. The method of claim 2, wherein the at least one antibody is anti-human CD66b.

5. The method of claim 2, wherein the at least one antibody is fluorescein isothiocyanate anti-human CD66b.

6. The method of claim 1, wherein the level of neutrophil-derived microparticles is determined via flow cytometry.

7. The method of claim 1, wherein the level of neutrophil-derived microparticles is determined via fluorescence-activated cell sorting.

8. The method of claim 3, wherein determining the level of neutrophil-derived microparticles comprises:
    (i) exposing the at least a portion of a biological sample from the patient contacted with reagents for detection and/or quantification of neutrophil-derived microparticles in step (a) to light of a single wavelength, wherein exposure of the light of the single wavelength thereto scatters the light and/or excites fluorescent chemicals in the at least a portion of the biological sample such that the fluorescent chemicals emit fluorescence; and
    (ii) detecting the light scattered and/or the fluorescence emitted by the fluorescent chemicals in step (i).

9. The method of claim 1, wherein an elevated level of neutrophil-derived microparticles is from about 750 neutrophil-derived microparticles/µL to about 2,500 neutrophil-derived microparticles/µL.

10. The method of claim 1, wherein the cutoff value of the neutrophil-derived microparticles is about 500 neutrophil-derived microparticles/µL.

11. The method of claim 1, wherein the biological sample is abdominal fluid.

12. The method of claim 1, wherein the patient is human.

13. The method of claim 1, wherein:
    the differential centrifugation comprises:
    (i) performing a first centrifugation of the biological sample at a first acceleration for a first time period, wherein the first centrifugation forms a first pellet and a first supernatant,
    (ii) performing a second centrifugation of the first supernatant at a second acceleration for a second time period, wherein the second centrifugation forms a second pellet and a second supernatant, and
    (iii) performing a third centrifugation of the second supernatant at a third acceleration for a third time period, wherein the third centrifugation forms a third pellet and a third supernatant, and wherein the third pellet comprises the microparticles.

14. The method according to claim 1, wherein the patient is treated with an antibiotic selected from the group consisting of penicillins, cephalosporins, polymixins, rifamycins, lipiarmycins, quinolones, sulfonamides, aminoglycosides, macrolides, tetracyclines, cyclic lipopeptides, glycylines, oxazolidinones, and combinations thereof.

15. The method according to claim 1, wherein the treating step (d) comprises a therapy selected from the group consisting of administering an antibiotic, administering intravenous fluids, surgical drainage, providing support for organ dysfunction, and combinations thereof.

* * * * *